United States Patent
Forsell

(10) Patent No.: US 9,883,934 B2
(45) Date of Patent: Feb. 6, 2018

(54) MECHANICAL ANAL INCONTINENCE APPARATUS

(71) Applicant: Peter Forsell, Zug (CH)

(72) Inventor: Peter Forsell, Zug (CH)

( * ) Notice: Subject to any disclaimer, the term of this patent is extended or adjusted under 35 U.S.C. 154(b) by 177 days.

(21) Appl. No.: 14/265,373

(22) Filed: Apr. 30, 2014

(65) Prior Publication Data

US 2015/0057490 A1     Feb. 26, 2015

Related U.S. Application Data

(60) Division of application No. 11/476,107, filed on Jun. 28, 2006, now Pat. No. 8,734,318, which is a continuation of application No. 10/269,949, filed on Oct. 15, 2002, now abandoned, which is a continuation of application No. 09/503,148, filed on Feb. 11, 2000, now Pat. No. 6,464,628.

(51) Int. Cl.
*A61F 2/00* (2006.01)
*A61N 1/378* (2006.01)

(52) U.S. Cl.
CPC .... *A61F 2/0036* (2013.01); *A61F 2250/0001* (2013.01); *A61N 1/3787* (2013.01)

(58) Field of Classification Search
CPC ...... A61F 2/004; A61F 2/0004; A61F 2/0022; A61F 2/0027; A61F 2/0031

USPC ................................................ 600/29–32, 37
See application file for complete search history.

(56) References Cited

U.S. PATENT DOCUMENTS

| | | | | |
|---|---|---|---|---|
| 4,711,231 A | * | 12/1987 | Finegold | A61F 2/0036 128/DIG. 25 |
| 4,786,276 A | * | 11/1988 | Haber | A61F 2/004 128/DIG. 26 |
| 4,941,461 A | * | 7/1990 | Fischell | A61F 2/26 52/2.21 |
| 5,593,443 A | * | 1/1997 | Carter | A61F 2/004 128/DIG. 25 |
| 5,738,628 A | * | 4/1998 | Sierocuk | A61B 17/3421 600/104 |
| 6,319,191 B1 | * | 11/2001 | Sayet | A61F 2/0036 600/29 |

* cited by examiner

*Primary Examiner* — Samuel Gilbert
(74) *Attorney, Agent, or Firm* — Gabriela B. Tomescu; Bergenstråhle & Partners AB

(57) ABSTRACT

An anal incontinence treatment apparatus with an adjustable restriction device implanted in a patient, who suffers from anal incontinence. The device engages a portion of the colon or rectum of the patient to restrict the fecal passageway. A hydraulic adjustment device adjusts the restriction device to restrict or release the fecal passageway, i.e. to normally close the fecal passageway and open the fecal passageway when the patient wants to relieve himself or herself.

22 Claims, 16 Drawing Sheets

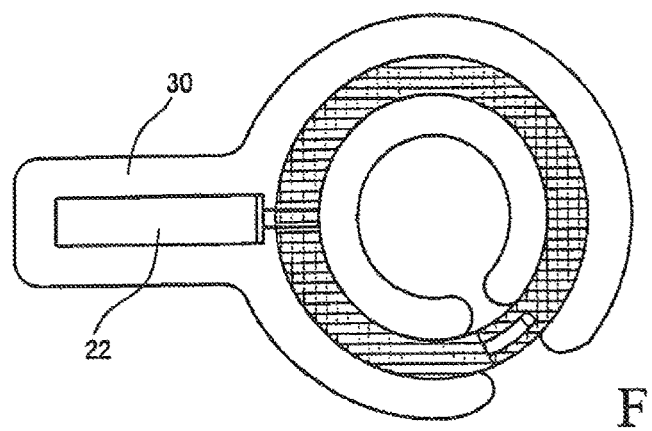
Fig. 4
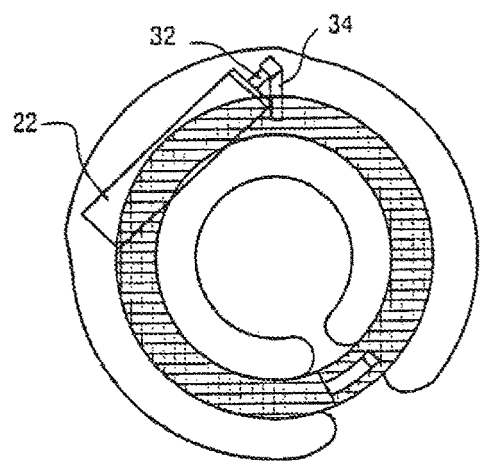
Fig. 5
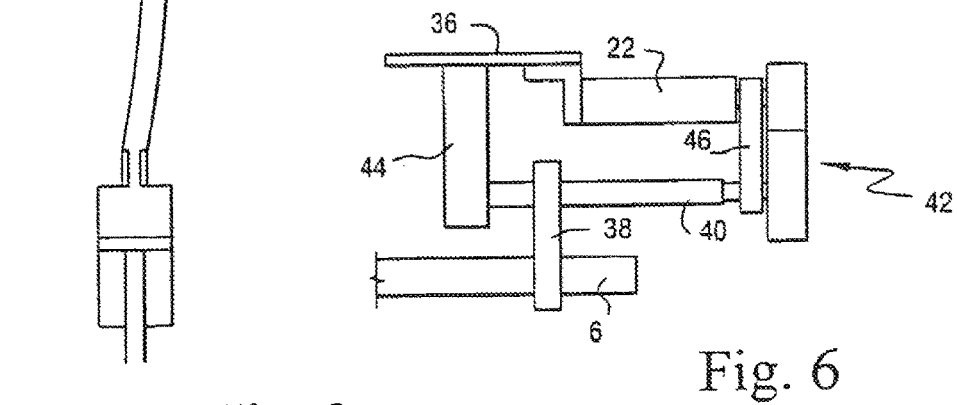
Fig. 8
Fig. 6

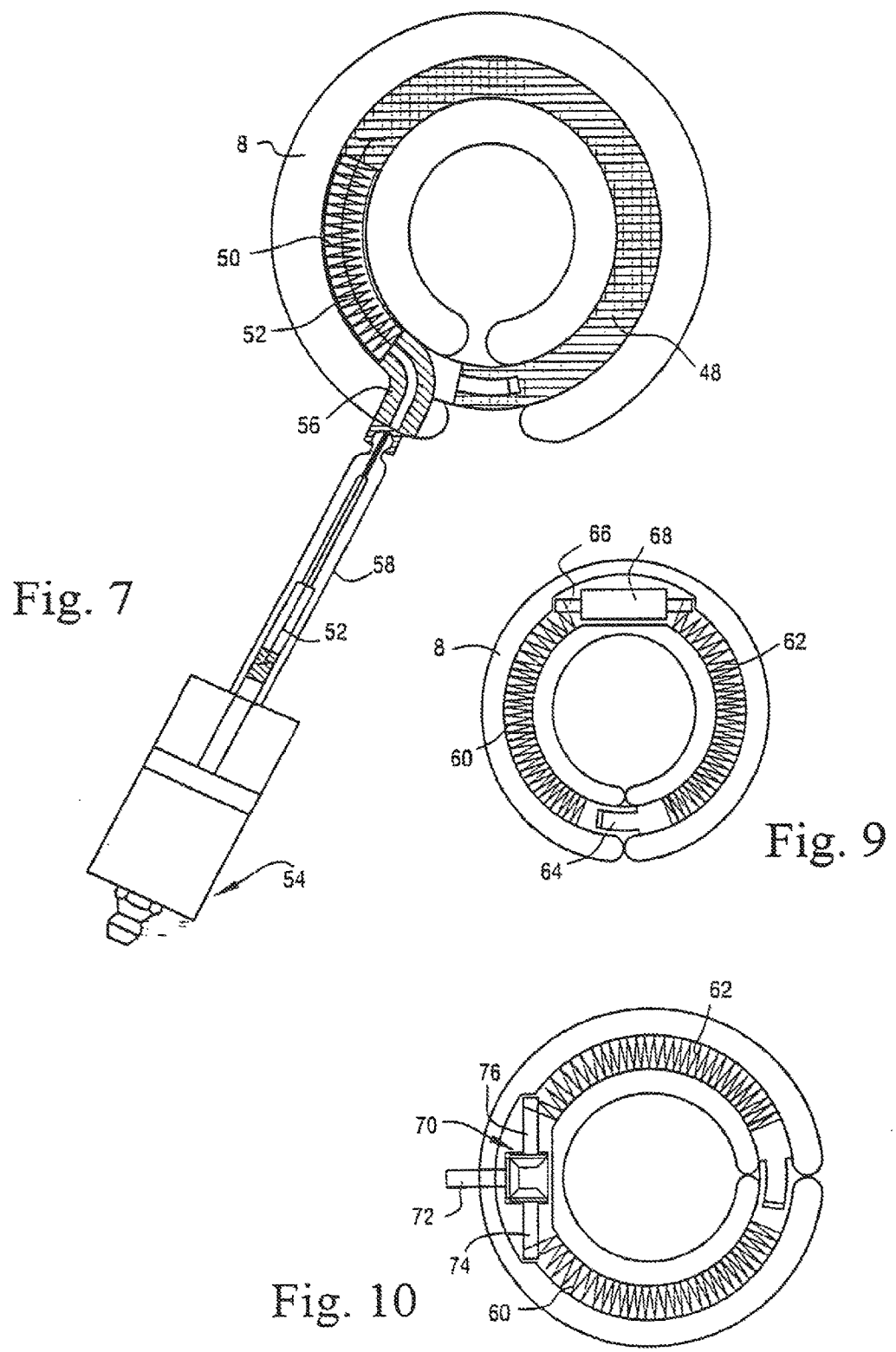

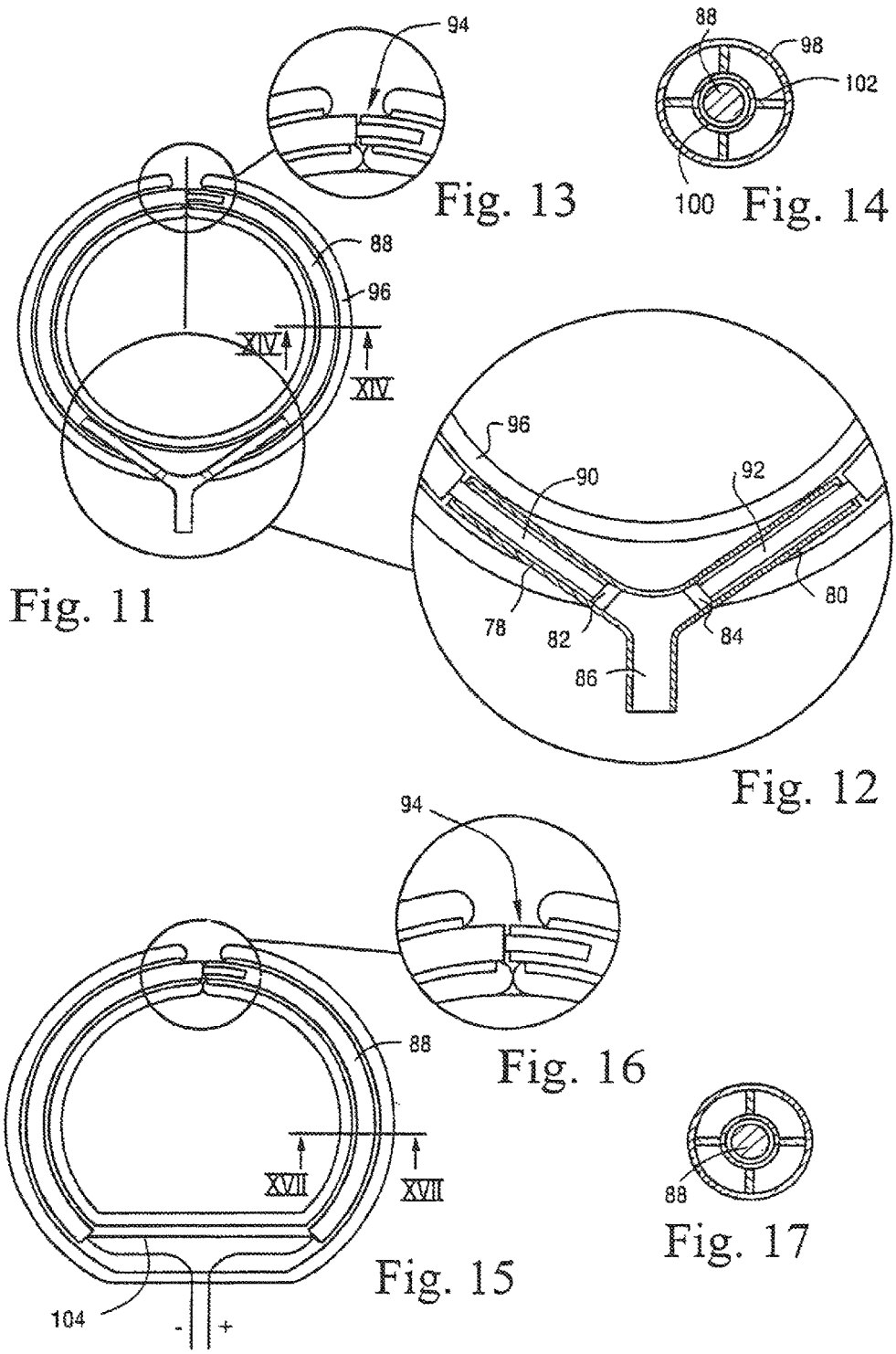

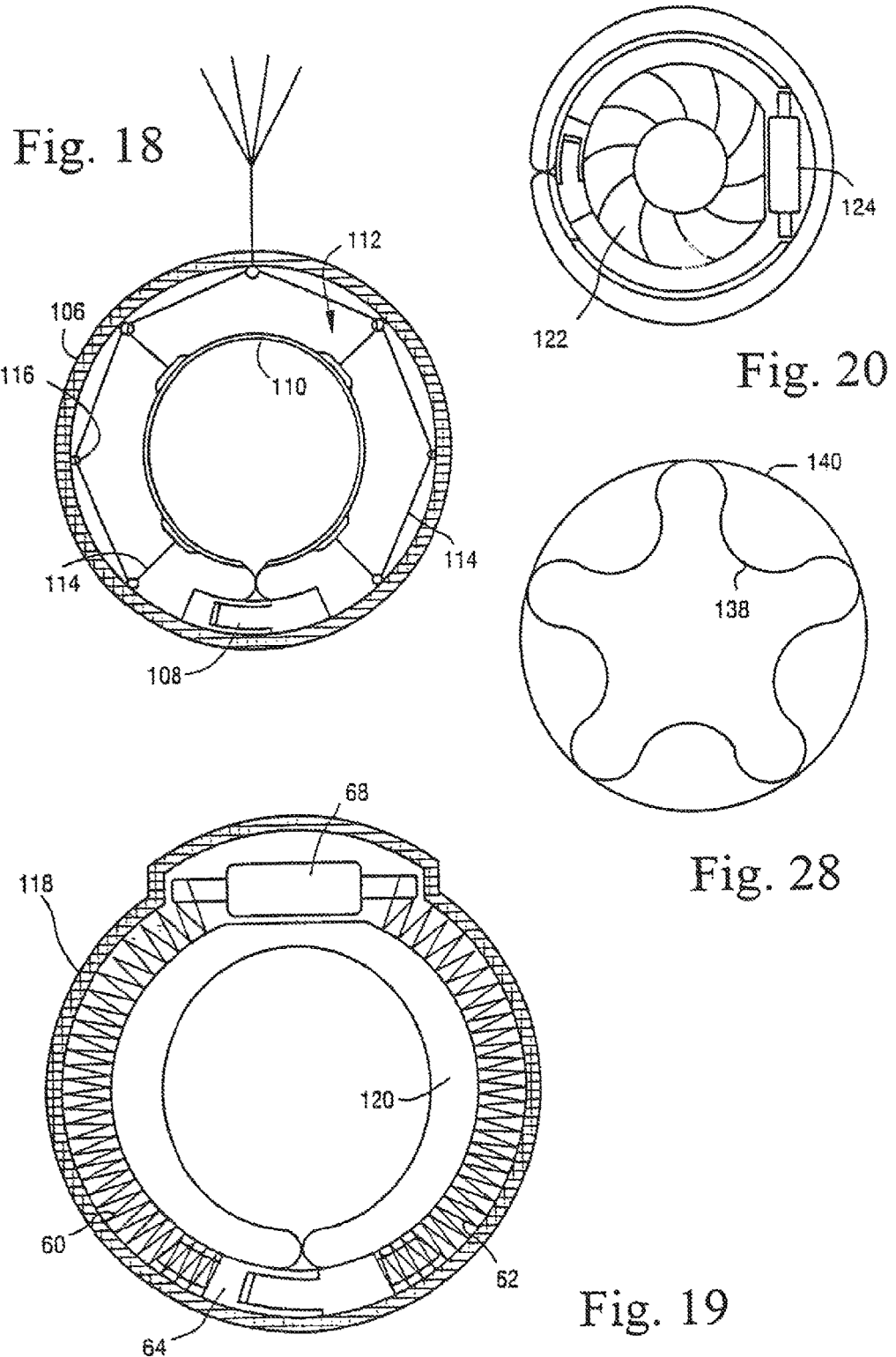

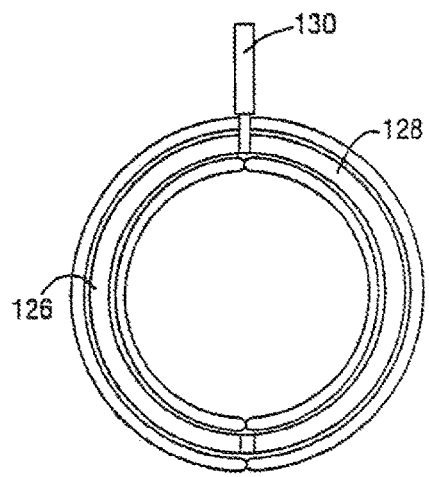
Fig. 21
Fig. 22
Fig. 23
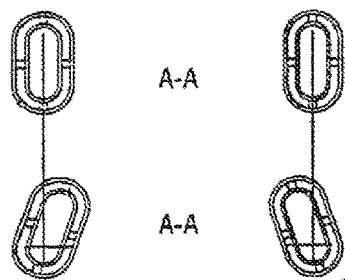
Fig. 26
Fig. 27
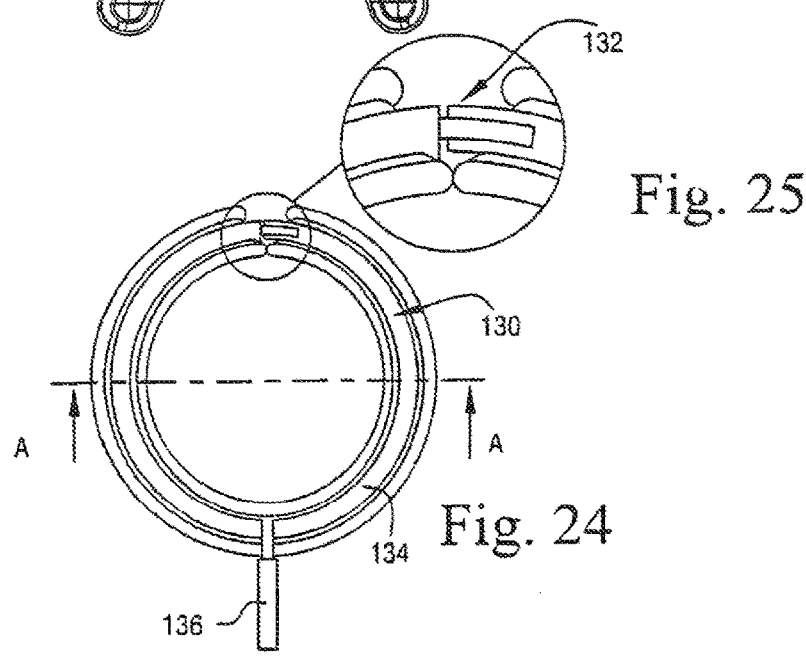
Fig. 25
Fig. 24

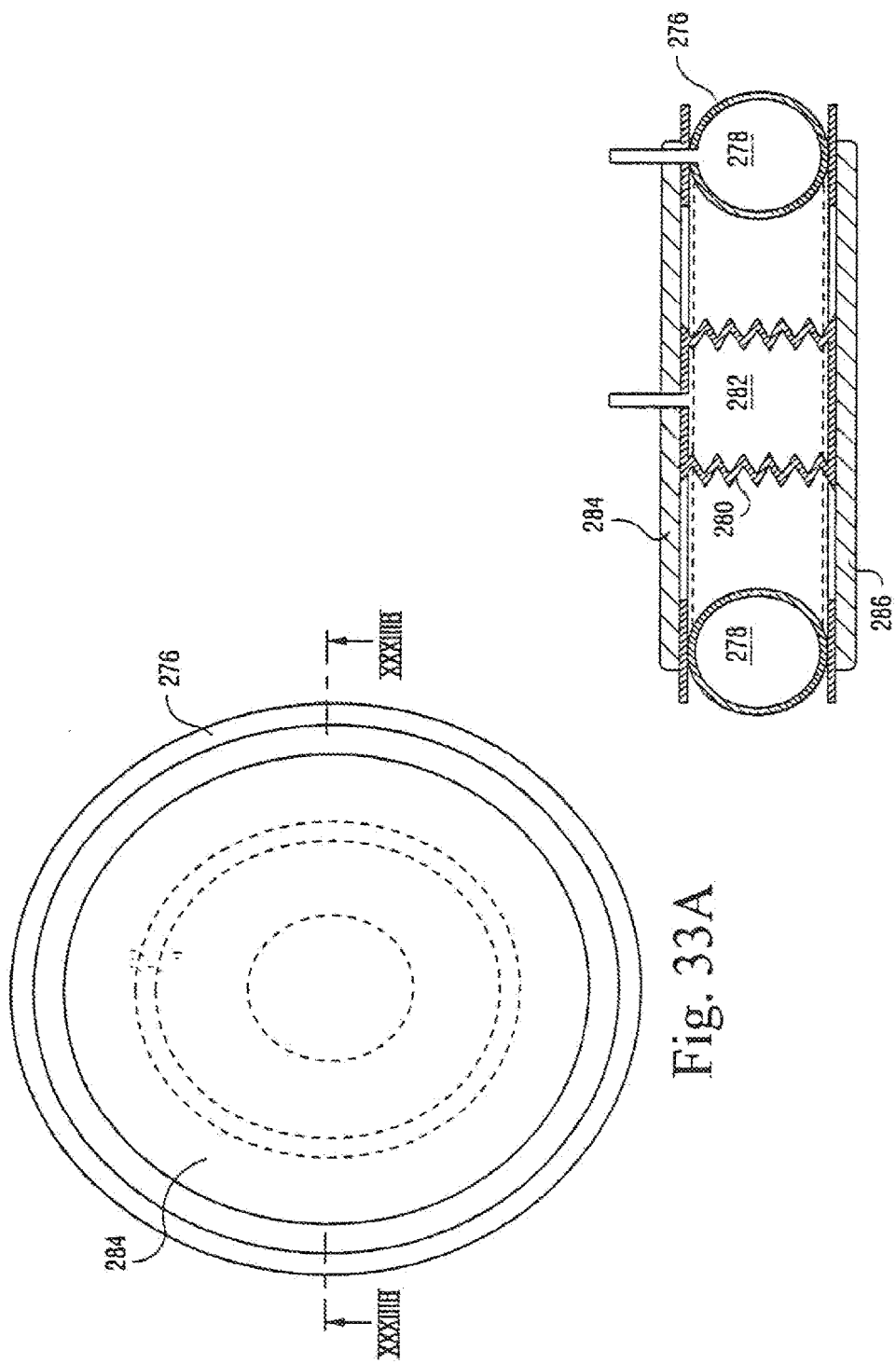

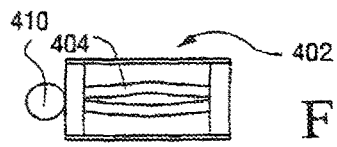
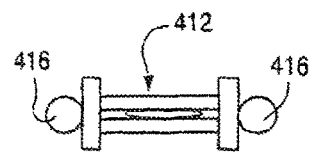
Fig. 36A
Fig. 37A
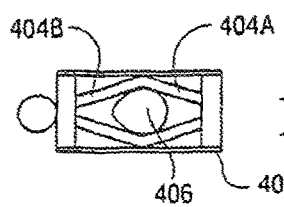
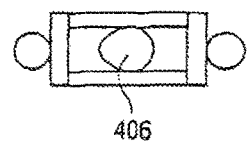
Fig. 36B
Fig. 37B
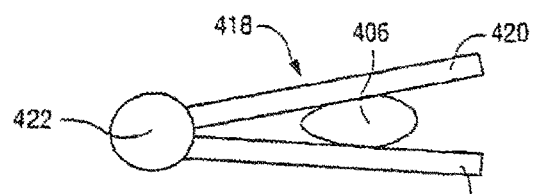
Fig. 38
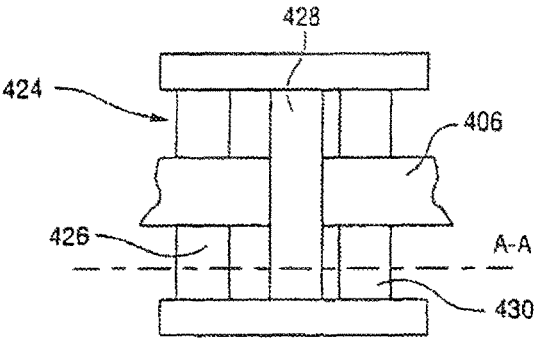
Fig. 39A
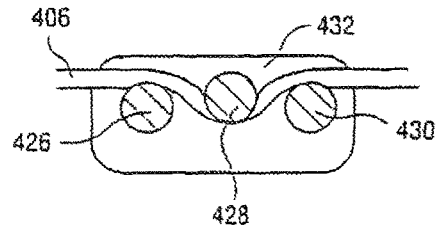
Fig. 39B
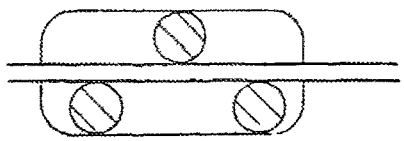
Fig. 39C

MECHANICAL ANAL INCONTINENCE APPARATUS

This application is a divisional of U.S. patent application Ser. No. 11/476,107,794, filed Jun. 28, 2006 which is a continuation of application Ser. No. 10/269,949, filed on Oct. 15, 2002, now abandoned, which is a continuation of application Ser. No. 09/503,148, filed on Feb. 11, 2000, now U.S. Pat. No. 6,464,628, the entire contents of which are hereby incorporated by reference in this application.

BACKGROUND OF THE INVENTION

The present invention relates to an anal incontinence treatment apparatus and method. More specifically, the invention relates to an anal incontinence treatment apparatus and method for surgical application in the body of an anal incontinence patient for restricting the colon or rectum of a patient.

Anal incontinence is a widespread problem. Many different solutions to this problem have been tried. Several kinds of sphincter plastic surgery are used today to remedy anal incontinence. There is a prior manually operated sphincter system in an initial clinical trial phase with the hydraulic sphincter system connected to a reservoir placed in the scrotum. Disadvantage of this system is that hard fibrosis created around the reservoir over time may cause malfunction of pumping components. Thus, the created fibrosis will sooner or later become a hard fibrotic layer which may make it difficult to pump the reservoir. Yet a further disadvantage is that the use of hydraulic fluid always entails a risk of fluid leaking from the prosthetis. Furthermore, it is a rather complicated task to mechanically manually pump the reservoir when defaecation is needed. U.S. Pat. No. 5,593,443 discloses hydraulic anal sphincter under both reflex and voluntary control. An inflatable artificial sphincter with the pump system in scrotum is disclosed in U.S. Pat. No. 4,222,377.

SUMMARY OF THE INVENTION

A prime object of the present invention is to provide an anal incontinence treatment apparatus and method in which the risk of liquid leakage within the patient's body is substantially reduced or completely eliminated.

A further object of the invention is to provide an anal incontinence treatment apparatus and method, which does not require a manual manipulation of a combined reservoir a pump mechanism in the scrotum or labia majora region of the patient.

Accordingly, the present invention provides an anal incontinence treatment apparatus, comprising:

an adjustable restriction device implanted in a patient, who suffers from anal incontinence, and engaging a portion of the colon or rectum of the patient to restrict the fecal passage-way therein, and an adjustment device which mechanically adjusts the restriction device to restrict or release the fecal passageway.

The adjustment device may be non-manually operated, i.e. the adjustment may be operated by any powered means, not manipulated by touching the skin of the patient. Preferably, the adjustment device adjusts the restriction device in non-invasive manner.

The adjustment device may adjust the restriction device in a non-magnetic manner, i.e. magnetic forces may not be involved when adjusting the restriction device. Furthermore, as opposed to prior art anal incontinence treatment devices the adjustment device of the invention is not operated by manual forces, such as by manually compressing a fluid containing balloon implanted in the scrotum. Instead the apparatus of the invention may further comprise a powered operation device for operating the adjustment device.

In the various embodiments hereinafter described the restriction device generally forms an at least substantially closed loop. However, the restriction device may take a variety of different shapes, such as the shape of a square, rectangle or ellipse. The substantially closed loop could for example be totally flat, i.e. thin as seen in the radial direction. The shape of restriction device may also be changed during use, by rotation or movements of the restriction device in any direction.

A physical lumen, like the colon or rectum or the prolongation thereof, is often easier to restrict by contracting at least two opposite or different side walls of the lumen against each other. The expression "colon or rectum or the prolongation thereof" should be understood to mean the rectum extended all the way out to the anal sphincter and following the passage of the large intestine in the other direction.

Either mechanical or hydraulic solutions may be employed to operate the restriction device. Alternatively, the restriction device may comprise an adjustable cuff, a clamp or a roller for bending the colon or rectum or the prolongation thereof to restrict the fecal passageway therein. Such a cuff, clamp or roller may also be utilized for squeezing the colon or rectum or the prolongation thereof against human material inside the body of the patient for an example the sacral bone of the patient.

Preferably, the restriction device comprises an elongated restriction member and forming means for forming the restriction member into at least a substantially closed loop around the portion of the tissue, the loop defining a restriction opening, whereby the adjustment device adjusts the restriction member in the loop to change the size of the restriction opening.

The restriction device may be implanted in the abdomen or retroperitoneum of the patient and preferably may engage the colon or rectum or the prolongation thereof.

The adjustment device may be incorporated in the restriction device as well as being controlled by hydraulic means.

In accordance with a preferred first adjustment principle, the adjustment device mechanically adjusts the longitudinal extension of the elongated restriction member in a loop form.

In a preferred embodiment of the invention utilizing the first adjustment principle, the restriction member comprises a main portion and two elongated end portions, and the adjustment device establishes longitudinal relative displacement between the end portions of the restriction member, so that the size of the restriction opening is adjusted. The forming means may comprise any suitable known or conventional device capable of practicing the desired function, such as a spring material forming the elongated restriction member into the loop, so that the restriction opening has a predetermined size, and the adjustment device may adjust the restriction member against the spring action of the spring material. In other words, the restriction member may comprise a spring clip. The spring material may be integrated in the restriction member.

Preferably, the adjustment device comprises a movement transferring member, suitably a drive wheel, in engagement with at least one of the end portions of the restriction member and operable to displace the one end portion relative to the other end portion of the restriction member.

The drive wheel may advantageously be in engagement with both of the end portions of the restriction member and be operable to displace said end portions relative to each other. An elongated flexible drive shaft may be operatively connected to the drive wheel, for transferring manual or motor generated power from a location remote from the restriction member. In its simplest embodiment, the drive wheel may comprise a pulley in frictional engagement with the restriction member. As an alternative, a gear rack may be formed on at least one of the end portions of the restriction member and the drive wheel may comprise a gear wheel in mesh with the gear rack. Other suitable known or conventional mechanisms may also or alternatively be used as the adjustment device.

The movement transferring member may alternatively comprise at least one cylinder and a piston, which is movable therein and is connected to one of the end portions of the restriction member, the piston being operable to longitudinally displace the one end portion of the restriction member relative to the other end portion of the restriction member. Alternatively, the movement transferring means may comprise two interconnected cylinders and two pistons in the respective cylinders connected to said end portions, respectively, of the restriction member, the pistons being operable to longitudinally displace the end portions of the restriction member relative to each other. Other known or conventional devices also or alternatively can be used as the movement transferring member.

A motor, which is fixed relative to the main portion of the restriction member and has a rotating drive shaft operatively connected to the movement transferring member, may be positioned relative to the elongated restriction member such that the drive shaft extends transverse thereto. Alternatively, the motor may be positioned relative to the elongated restriction member such that the drive shaft extends substantially tangentially to the loop of the restriction member.

In another embodiment of the invention utilizing the first adjustment principle, the elongated restriction member is longitudinally resilient and the adjustment device comprises a contraction device for longitudinally contracting the resilient restriction member. Preferably, the elongated restriction member comprises a substantially nonresilient main portion and an end portion forming an elongated helical spring, which is contractable by the contraction device. The contraction device may suitably comprise an elongated flexible pulling member connected to the main portion of the restriction member and extending through the helical spring to contract the helical spring against an arresting member, which is fixed relative to the main portion of the restriction member. The pulling member may extend in an elongated tube joined at one end thereof to the arresting member, so that a motor remote from the restriction member may be attached to the other end of the elongated tube and pulls the pulling member through the tube to contract the helical spring.

In yet another embodiment of the invention utilizing the first adjustment principle, the elongated restriction member comprises an elongated helical spring having a free end, and a body to which the spring is nonrotatably secured at its opposite end. The adjustment device rotates the helical spring in one direction to enlarge the coils of the helical spring to longitudinally contract the spring and to rotate the spring in the opposite direction to reduce the size of the coils of the spring to longitudinally extend the spring. As a preferred alternative, the restriction member comprises a further elongated helical spring having a free end and nonrotatably secured to the body at its opposite end, and the adjustment device comprises a drive shaft having two opposite end portions connected to the springs, respectively, at their free ends, the helical coils forming left and right hand helices, respectively. The adjustment device may alternatively comprise a gearing having an input shaft and two opposite aligned output shafts connected to the helical springs, respectively, at their free ends, the input shaft being connected to said output shafts so that the output shafts rotate in the opposite directions upon rotation of the input shaft, the helical coils forming the same helices.

In accordance with a second adjustment principle, the adjustment device mechanically adjusts the restriction member so that at least a portion of a radially innermost circumferential confinement surface formed by the restriction member is substantially radially displaced.

In one embodiment of the invention utilizing the second adjustment principle, the restriction member comprises an elongated voltage responsive element forming part of the confinement surface and capable of bending into a bow in response to a voltage applied across the element, the radius of curvature of the bow being adjustable by changing the level of the voltage.

In another embodiment of the invention utilizing the second adjustment principle, the adjustment device changes the diameter of an elastic annular element of the restriction member, which forms the confinement surface. Preferably, the forming means comprises a substantially rigid outer annular element coaxially surrounding the elastic annular element, and the adjustment device comprises means for pulling the elastic annular element radially outwardly towards the outer annular element to expand the elastic annular element. For example, the pulling means may comprise a plurality of threads secured to the elastic annular element along the circumference thereof and running from the elastic annular element via guide members attached to the outer annular element.

In yet another embodiment of the invention utilizing the second adjustment principle, the forming means comprises a substantially rigid outer annular element, and the restriction member comprises an elongated helical spring extending internally along the outer annular element and contacting the latter. The helical spring forms part of the circumferential confinement surface and has a free end. The restriction member further comprises a body to which the spring is nonrotatably secured at its opposite end. The adjustment device rotates the helical spring in one direction to enlarge the coils of the spring to contract the circumferential confinement surface and rotates the spring in the opposite direction to reduce the size of the coils of the spring to expand the circumferential confinement surface. As an alternative, which is preferred, the restriction member comprises two elongated helical springs forming part of the circumferential confinement surface and connected to the body of the restriction member. The adjustment device rotates each spring in one direction to enlarge the coils of the spring to contract the circumferential confinement surface and rotates the spring in the opposite direction to reduce the size of the coils of the spring to expand the circumferential confinement surface.

In accordance with a third adjustment principle, the restriction member comprises at least two separate elements, at least one of which is pivoted so that it may turn in a plane in which the restriction member extends, and the adjustment device turns the pivoted element to change the size of the restriction opening. Preferably, the restriction member comprises a plurality of separate pivoted elements disposed in series, each pivoted element being turnable in the plane, and the adjustment device turns all of the pivoted elements to change the size of the restriction opening. For example, the pivoted elements may comprise lamellae arranged like the conventional adjustable aperture mechanism of a camera.

In accordance with a fourth adjustment principle, the adjustment device folds at least two foldable frame elements of the restriction member towards each other. Preferably, the foldable frame elements comprise two substantially or partly semi-circular frame elements which are hinged together so that the semi-circular elements are swingable relative to each other from a fully open state in which they form part of a circle to a fully folded state in which they form part of a semi-circle. The same principal may be used with the swingable parts mounted together in one end and not in the other end. Alternatively, the restriction device may comprises two preferable rigid articulated clamping elements positioned on opposite or different sides of colon rectum or the prolongation thereof, and the adjustment device turns the clamping elements toward each other to clamp the colon or rectum or the prolongation thereof between the clamping elements, thereby restricting the fecal passageway in the colon or rectum or the prolongation thereof.

In accordance with a fifth adjustment principle, the adjustment device turns the restriction member around a longitudinal extension thereof, the elongated restriction member being elastic and varying in thickness as seen in a cross-section therethrough. Suitably, the elongated restriction member comprises an elastic belt.

In accordance with a sixth adjustment principle, the adjustment device changes the size of the restriction opening such that the outer circumferential confinement surface of the restriction member is changed.

In accordance with a seventh adjustment principle, the adjustment device changes the size of the restriction opening such that the outer circumferential confinement surface of the restriction member is unchanged.

In accordance with an eighth adjustment principle, the elongated restriction member may be flexible, and the adjustment device pulls a first portion of the flexible restriction member from a second portion of the flexible restriction member opposite the first portion in the loop to squeeze the colon or rectum or the prolongation thereof between the opposite lengths of the elongated flexible restriction member to restrict the fecal passageway in the colon or rectum or the prolongation thereof.

In accordance with a ninth adjustment principle, the restriction device comprises at least two elements on opposite or different sides of the colon or rectum or the prolongation thereof, and the adjustment device decreases the distance between the elements to squeeze the colon or rectum or the prolongation thereof between the elements, thereby restricting the fecal passageway in the colon or rectum or the prolongation thereof. It is also possible to use only one element and squeeze the colon or rectum or the prolongation thereof against human bone or tissue. The elements above may as well as all the restriction members mentioned in this application be everything from rigid to soft.

In accordance with a tenth adjustment principle, the restriction device bends or rotates a portion of colon or rectum or the prolongation thereof to restrict the fecal passageway in the same. For example, the restriction device may comprise at least two bending members, such as cylindrical or hour-glass shaped rollers, positioned on opposite or different sides of the colon or rectum or the prolongation thereof and displaced relative to each other along the colon or rectum or the prolongation thereof, and the adjustment device may move the bending members against the colon or rectum thereof to bend the latter to restrict the fecal passageway in the colon or rectum or the prolongation thereof Suitably, the displacement members may comprise rollers. The restriction device may also rotate a portion of the esophagus or stomach. The bending or rotating members may have any shape or form and be either hydraulic or non-inflatable.

Two holding members one placed more distal than the other comprising two at least substantially closed loops may be rotated in opposite direction to each other. With interconnecting material for example flexible bands between the holding members a restriction will occur between the holding members when they are rotated.

The restriction device may in all applicable embodiments have any shape or form and be either hydraulic or non-inflatable.

In all of the above-described embodiments of the invention the adjustment device is conveniently operated by any suitable motor, preferably an electric motor, which may be fixed directly to or be placed in association with the restriction device, or alternatively be located remote from the restriction device, advantageously in the abdomen or pelvic region or subcutaneously or in the retroperitoneum of the patient. In the latter alternative the motor is advantageously connected to the adjustment device by a flexible power transmission conduit to permit a suitable positioning of the motor in the abdomen of the patient. The motor may be manually activatable, for example by an implanted switch.

In some of the above described embodiments of the invention, however, the adjustment device may conveniently be operable by a hydraulic operation device, which preferably is manually activatable. The hydraulic operation device may advantageously include hydraulic servo means to facilitate manual activation. As an alternative, the hydraulic device may be powered by an electric motor, which may be manually activatable or controlled by remote control means. The components of such a hydraulic operation device may be placed in association with the restriction device and/or be located at a suitable place in the abdomen or subcutaneously.

More specifically, a reservoir may be provided containing a predetermined amount of fluid for supplying the hydraulic operation device with fluid. The reservoir defines a chamber for the predetermined amount of fluid and the hydraulic operation device changes the size of the chamber. The hydraulic operation device may comprise first and second wall portions of the reservoir, which are displaceable relative to each other to change the size of the chamber of the reservoir. The first and second wall portions of the reservoir may be designed to be displaceable relative to each other by manual manipulation thereof, preferably to permit manual pushing, pulling or rotation of any of the wall portions in one direction. Alternatively, the wall portions may be displaceable relative to each other by magnetic means (such as a permanent magnet and magnetic material reed switch, or other known or conventional magnetic devices), hydraulic means or electrical control means such as an electric motor. The magnetic means, hydraulic means, or electrical control means may all be activated by manual manipulation, preferably using a subcutaneously located manually manipulatable device. This control may be indirect, for example via a switch.

The hydraulic operation device may operate the adjustment device with fluid from the reservoir in response to a predetermined first displacement of the first wall portion of the reservoir relative to the second wall portion of the reservoir, to adjust the restriction device to release the tissue, and to operate the adjustment device with fluid from the reservoir in response to a predetermined second displacement of the first wall portion of the reservoir relative to the second wall portion of the reservoir, to adjust the restriction device to restrict the blood flow leaving the penis. In this embodiment, no pump is used, only the volume of the reservoir is varied. This is of great advantage compared to the solution described below when a pump is used to pump fluid between the reservoir and the adjustment device because there is no need for a non-return valve and it is still possible to have fluid going both to and from the reservoir.

As an alternative, the hydraulic operation device may comprise an activatable pump for pumping fluid between the reservoir and the adjustment device. The pump may pump fluid both to and away from the adjustment device, or hydraulic means controlling the adjustment device. A mechanical manual solution is proposed in which it is possible to pump in both directions just by pushing an activating member in one direction. Another alternative is a pump pumping in only one direction and an adjustable valve to change the direction of fluid to either increase or decrease the amount of fluid in the reservoir. This valve may be manipulated manually, mechanically, electrically, magnetically, or hydraulically. Any kind of motor could of course be used for all the different operations as well as wireless remote solutions. The pump may comprise a first activation member for activating the pump to pump fluid from the reservoir to the adjustment device and a second activation member for activating the pump to pump fluid from the adjustment device to the reservoir. The activation members may be operable by manual manipulation, preferably to permit manual pushing, pulling or rotating thereof in one direction. Suitably, at least one of the activation members is adapted to operate when subjected to an external pressure exceeding a predetermined magnitude.

Alternatively, at least one of the first and second activating members may be operable by magnetic means, hydraulic means or electrical control means such as an electric motor. The magnetic means, hydraulic means, or electrical control means may all be activated by manual manipulating means preferably located subcutaneously. This activation may be indirect, for example via a switch.

Advantageously, especially when manual manipulation means are used, a servo system could be used. With servo means less force is needed for controlling the adjustment device. Hydraulic means is preferably used with servo means. One example is a closed system that controls another closed system in which the hydraulic devices of the adjustment device is incorporated. Minor changes in the amount of fluid in a reservoir of the first system could then lead to major changes in the amount of fluid in a reservoir in the second system. In consequence, the change of volume in the reservoir of the second system affects the hydraulic device of the adjustment device, which is incorporated in the second closed system. The great advantage of this servo system is that the larger volume system could be placed inside the abdomen or retroperitoneum where there is more space and still would be possible to use manual manipulation means of the smaller system subcutaneously. The servo reservoir could control the reservoir of the larger volume. The servo reservoir could be controlled directly or indirectly by a fluid supply means. The fluid supply means may be a small reservoir, which may be placed subcutaneously and may be activated by manual manipulation means controlling the servo reservoir.

Preferably, the servo means comprises hydraulic means and a servo reservoir and eventually a fluid supply reservoir. Both reservoirs define a chamber containing servo fluid, and the hydraulic means comprises first and second wall portions of the servo reservoir, which are displaceable relative to each other to change the size of the chamber of the servo reservoir. The hydraulic means may control the adjustment device indirectly, e.g. via an increased amount of fluid in the servo reservoir, in response to a predetermined first displacement of the first wall portion of any of the reservoirs relative to the second wall portion of the reservoir to restrict blood flow leaving the penis, and to control the adjustment device in response to a second displacement of the first wall portion of any reservoir relative to the second wall portion, to indirectly adjust the restriction device to release the tissue. The wall portions of the reservoirs may be designed to be displaceable relative to each other by manual manipulation thereof or be displaceable relative to each other by manually pushing, pulling or rotating any of the wall portions of the reservoir in one direction. Alternatively, the wall portions of the servo reservoir may be displaceable relative to each other by magnetic means, hydraulic means or electric control means including an electric motor.

The magnetic means, hydraulic means, or electrical control means may all be activated by manually manipulated means preferably located subcutaneously. This control may be indirect for example via a switch.

Even in the broadest embodiment of the invention the adjustment device may comprise a servo means. The servo means may comprise a hydraulic operation means, an electrical control means, a magnetic means, mechanical means or a manual manipulation means. The hydraulic operation means, electrical control means, mechanical means or magnetic means may be activated by manual manipulating means. Using a servo system will save the use of force when adjusting the adjustment device which may be of importance in many applications, for example when a battery cannot put out enough current although the total energy in the battery is more than enough to power the system.

All solutions may be controlled by a wireless remote control for controlling the adjustment device. The remote control may advantageously be capable of obtaining information related to the fecal passageway or the pressure against the restriction device or colon or rectum or other important physical parameters and of commanding the adjustment device to adjust the restriction device in response to obtained information. With the wireless remote control the apparatus of the invention is conveniently controlled by the patient when he so desires, which is of great advantage compared to the prior art procedures. With the remote control the apparatus of the invention is conveniently controlled to adjust the implanted restriction device, which controls the defaecation. The restriction device may be operable to open and close fecal passageway. The restriction device may steplessly control the cross-sectional area of the passageway.

The apparatus may further comprise a pressure sensor for directly or indirectly sensing the pressure against the restriction device and the restriction device may control the blood flow in response to signals from the pressure sensor. The pressure sensor may be any suitable known or conventional pressure sensor such as shown in U.S. Pat. Nos. 5,540,731, 4,846,181, 4,738,267, 4,571,749, 4,407,296 or 3,939,823; or an NPC-102 Medical Angioplasty Sensor. The adjustment device preferably non-invasively adjusts the restriction device to change the size of the cross-sectional area.

The adjustment device and/or other energy consuming components of the apparatus may be energised with wirelessly transmitted energy from outside the patient's body or be powered by an implanted battery or accumulator.

The apparatus may further comprise an implanted energy transfer device for transferring wireless energy directly or indirectly into kinetic energy for operation of the restriction device.

The wireless remote control may comprise means for wireless transfer of energy from outside the patient's body to energy consuming implantable components of the apparatus. A motor may suitably be implanted in the patient for operating the adjustment device and the means for wireless transfer of energy may directly power the motor with transferred energy. The energy transferred by the means for transfer of energy may comprise any suitable kind of energy signals including wave signals, an electric field or a magnetic field.

Preferably, the wireless remote control comprises a separate signal transmitter or receiver and a signal receiver or transmitter implanted in the patient. For example, the signal transmitter and signal receiver may transmit and receive a signal in the form of digital pulses, which may comprise a magnetic or electric field. Alternatively, which is preferred, the signal transmitter and signal receiver may transmit and receive an electromagnetic wave signal, a sound wave signal or a carrier wave signal for a remote control signal. The receiver may comprise an implanted control unit for controlling the adjustment device in response to a control signal from the signal transmitter.

The apparatus of the invention may further comprise an implanted energizer unit for providing energy to energy consuming implanted components of the apparatus, such as electronic circuits and/or a motor for operating the adjustment device. The control unit may power such an implanted motor with energy provided by the energizer unit in response to a control signal received from the signal transmitter. Any known or conventional signal transmitter or signal receiver that is suitable for use with a human or mammal patient may be provided as the signal transmitter or signal receiver of the invention. Generally, the signals may comprise electromagnetic waves, such as infrared light, visible light, laser light, micro waves, or sound waves, such as ultrasonic waves or infrasonic waves, or any other type of wave signals. The signals may also comprise electric or magnetic fields, or pulses. All of the above-mentioned signals may comprise digital signals. The control signals may be carried by a carrier wave signal, which in an alternative embodiment may be the same signal as the wireless energy signal. Preferably a digital control signal may be carried by an electromagnetic wave signal. The carrier wave or control signal may be amplitude or frequency modulated.

The motor may be any type of motor, such as a pneumatic, hydraulic or electric motor and the energizer unit may power the motor with pressurized gas or liquid, or electric energy, depending on the type of motor. Where the motor is an electric motor, it may power pneumatic or hydraulic equipment.

The energizer unit may comprise a power supply and the control unit may power the motor with energy from the power supply. Preferably, the power supply is an electric power supply, such as a battery, and the motor is an electric motor. In this case, the battery also continuously powers at least part of the circuitry of the signal receiver in a standby mode between the adjustments, in order to keep the signal receiver prepared for receiving signals transmitted from the signal transmitter.

The energizer unit may transfer energy from the control signal, as the control signal is transmitted to the signal receiver, into electric energy for powering the implanted electronic components. For example, the energizer unit may transfer the energy from the control signal into a direct or alternating current.

In case there is an implanted electric motor for operating the adjustment device the energizer unit may also power the motor with the transferred energy. Advantageously, the control unit directly powers the electric motor with electric energy, as the energizer unit transfers the signal energy into the electric energy. This embodiment is particularly simple and does not require any recurrent invasive measures for exchanging empty power supplies, such as batteries, that is required in the first embodiment described above.

For adjustment devices of the type that requires more, but still relatively low, power for its operation, the energizer unit may comprise a rechargeable electric power supply for storing the electric energy obtained and the control unit may power the electric motor with energy from the rechargeable electric power supply in response to a control signal received from the signal transmitter. In this case, the rechargeable power supply can be charged over a relatively long time (e.g. a few seconds up to a half hour) without powering the electric motor.

The electric power supply suitably comprises an inexpensive simple capacitor. In this case, the electric motor may be a stepping motor. In all embodiments the motor may preferable be able to perform a reversing function.

The signal transmitter may transmit an electromagnetic signal and the energizer unit may draw radiant energy from the electromagnetic wave signal, as the latter is transmitted to the signal receiver, and transfer the radiant energy into electric energy.

Alternatively, the energizer unit may comprise a battery or accumulator, an electrically operable switch adapted to connect the battery to the signal receiver in an on mode when the switch is powered and to keep the battery disconnected from the signal receiver in a standby mode when the switch is unpowered, and a rechargeable electric power supply for powering the switch. The control unit may power the electric motor with energy from the battery in response to a control signal received from the signal transmitter, when the switch is in its on mode. Advantageously, the energizer unit may transfer wave energy from the control signal, as the latter is transmitted to the signal receiver, into a current for charging the rechargeable electric power supply, which suitably is a capacitor. Energy from the power supply is then used to change the switch from off (standby mode) to on. This embodiment is suited for adjustment devices of the type that require relatively high power for their operation and has the advantage that the electronic circuitry of the signal receiver does not have to be powered by the battery between adjustments. As a result, the life-time of the battery can be significantly prolonged. The switch may be switched with magnetic, manual or electric energy.

As an example, the signal transmitter may transmit an electromagnetic wave signal and the energizer unit may draw radiant energy from the electromagnetic wave signal, as the latter is transmitted to the signal receiver, and may transfer the radiant energy into said current. The energizer unit suitably comprises a coil of the signal receiver for inducing an alternating current as the electromagnetic wave signal is transmitted through the coil and a rectifier for rectifying the alternating current. The rectified current is used for charging the rechargeable power source.

Alternatively, the signal transmitter and receiver may solely be used for a control signal and a further pair of signal transmitter and receiver may be provided for transferring signal energy to implanted components. By such a double system of signal transmitters and receivers the advantage is obtained that the two systems can be designed optimally for their respective purposes, namely to transmit a control signal and to transfer energy from an energy signal. Accordingly, the apparatus may further comprise an external energy transmitter for transmitting wireless energy, wherein the energizer unit comprises a battery and an operable switch for connecting the battery to the signal receiver in an on mode when the switch is powered and for keeping the battery disconnected from the signal receiver in a standby mode when the switch is unpowered, and the external energy transmitter powers the switch. Suitably, the energy transmitter may directly power the switch with the wireless energy to switch into the on mode. As should be realized by a skilled person, in many of the above-described embodiments of the invention the adjustment device may be operated by control means or manual manipulation means implanted under the skin of the patient, such as a pump, an electrical switch or a mechanical movement transferring means. In the manual embodiment it is not necessary to use a motor for operating the adjustment device.

In embodiments including hydraulic transmission means, an injection port connected to the hydraulic means may be provided for enabling, normally single, once-and-for-all, calibration of the amount of fluid in the hydraulic system.

In all embodiments a motor may be operatively connected to the adjustment device. A reversing device may be implanted in the patient for reversing the motor. The adjustment device preferably adjusts the restriction device in a non-manual manner without the patient touching his skin.

The restriction device is operable to open and close the fecal passageway steplessly and preferable controlled with a remote control. Preferably, a pressure sensor is used for directly or indirectly sensing the pressure against the restriction device or the colon or the rectum to prevent any necrosis of the human tissue. The restriction device may preferably be controlled in response to signals from the pressure sensor. The motor which preferably is used to adjust the restriction device must then be capable of performing a reversible function, that is to say reversed direction of the motor. Preferably the adjustment device may be energised directly with wirelessly transmitted energy from outside the patient's body. Preferable, the implanted energy transfer device transfers wireless energy directly or indirectly into kinetic energy for operation of the restriction device. In another embodiment it would also be possible to use an implanted accumulator or battery and control this implanted energy source from outside the patient's body to supply energy to the adjustment device or other energy consuming parts of the implanted apparatus.

The invention also provides a method for treating a patient suffering from anal incontinence comprising surgically implanting in the body of the an adjustable restriction device which directly engages the colon or rectum like an artificial sphincter around the fecal passageway therein, normally closed, and when desired, mechanically adjusting the restriction device to temporarily open the fecal passageway.

The adjustable restriction device may preferably be implanted in the base or prolongation of the patients rectum. It is possible to use one or several restricting devices engages the colon or rectum.

In accordance with the invention, there is further provided a method for treating anal incontinence, comprising the steps of placing at least two laparascopical trocars in the body of a patient suffering from anal incontinence, inserting a dissecting tool through the trocars and dissecting an area of the colon or rectum in the abdominal or pelvic or retroperitoneal surroundings, placing at least one adjustable restriction device in the dissected area engaging the rectum or colon, adjusting the restriction device to normally restrict the fecal passageway in the rectum or colon to substantially prevent the passage of fecal materials therethrough, and adjusting the restriction device to open the fecal passageway to allow the passage of fecal material therethrough when the patient wants to relieve himself or herself. A mechanically adjustable restriction device may be used when practicing this method, preferably in a non-manual manner, i.e. without touching subcutaneously implanted components of the apparatus.

The method may further comprise implanting a source of energy in the patient and providing a control device for controlling the source of energy from outside the patient's body to supply energy to the restriction device.

It should generally be understood that all the above embodiments may be combined in any working combination.

BRIEF DESCRIPTION OF THE DRAWINGS

FIGS. 4 and 5 schematically show two alternative designs of the embodiment of FIG. 1;

FIG. 6 schematically illustrates a motor arrangement for the design according to FIG. 5;

FIG. 7 is a schematic sectional view of a second embodiment of the apparatus in accordance with the invention;

FIG. 8 schematically illustrates a hydraulic transmission conduit for the embodiment of FIG. 7;

FIG. 9 is a schematic sectional view of a third embodiment of the apparatus in accordance with the invention;

FIG. 10 is a modification of the embodiment of FIG. 9;

FIG. 11 is a schematic view of a fourth embodiment of the apparatus in accordance with the invention;

FIGS. 12 and 13 are enlarged details of the embodiment of FIG. 11;

FIG. 14 is a cross-section along the line XIV-XIV of FIG. 11;

FIG. 15 is a schematic view of a fifth embodiment of the apparatus in accordance with the invention;

FIG. 16 is an enlarged detail of FIG. 15;

FIG. 17 is a cross-section along the line XVII-XVII of FIG. 15;

FIGS. 18 to 21 are schematic sectional views of a sixth, seventh, eighth and ninth embodiments, respectively, of the apparatus in accordance with the invention;

FIGS. 22 and 23 illustrate a fully open and a reduced restriction opening, respectively, of the embodiment of FIG. 21;

FIG. 24 is a schematic view of a tenth embodiment of the apparatus in accordance with the invention;

FIG. 25 is an enlarged detail of the embodiment of FIG. 24;

FIGS. 26 and 27 illustrate a fully open and a reduced restriction opening, respectively, of the embodiment of FIG. 24;

FIG. 28 schematically illustrates a cushion arrangement for protecting the tissue of the patient;

FIG. 33A is a front view of a hydraulic, pneumatic or mechanical servo system in accordance with a particular embodiment of the principal embodiment shown in FIG. 29D;

FIG. 33B is a cross-sectional view taken along line VB-VB of FIG. 33A;

FIGS. 36A and 36B are schematic views of an eleventh embodiment of the apparatus in accordance with the invention;

FIGS. 37A and 37B are schematic views of a twelfth embodiment of the apparatus in accordance with the invention;

FIG. 38 is a schematic view of a thirteenth embodiment of the apparatus in accordance with the invention;

FIGS. 39A, 39B and 39C are a schematic front view and schematic sectional views, respectively, of a fourteenth embodiment of the apparatus in accordance with the invention;

DETAILED DESCRIPTION OF THE DRAWINGS

Figures 1, 2, 3:
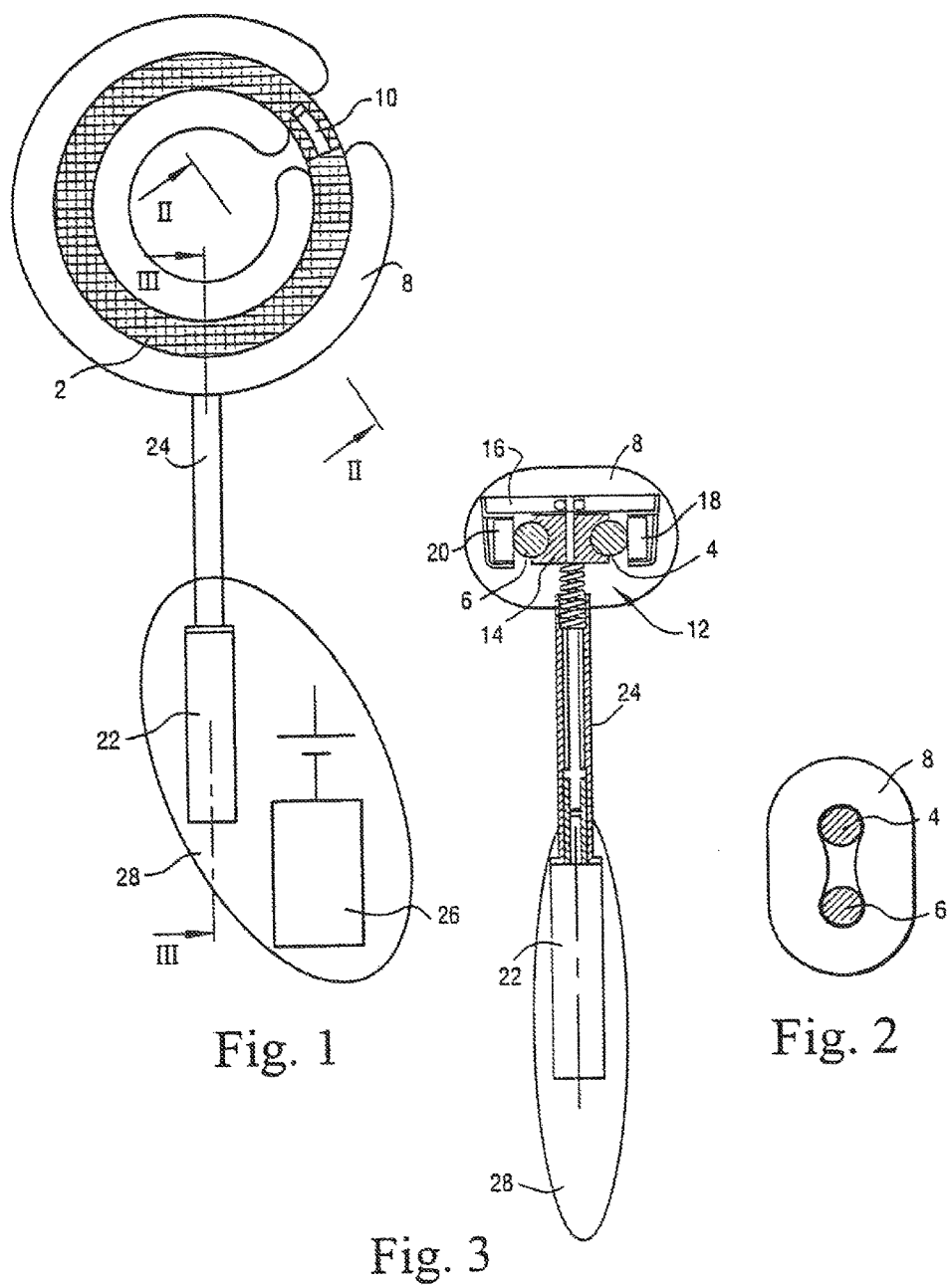
FIG. 1 is a schematic sectional view of a preferred first embodiment of the anal incontinence treatment apparatus in accordance with the invention.
FIGS. 2 and 3 are cross-sectional views taken along the lines II-II and III-III, respectively, of FIG. 1.

Referring to the drawing FIGURES, like reference numerals designate identical or corresponding elements throughout the several FIGURES.

FIGS. 1-3 show a preferred embodiment of the anal incontinence treatment apparatus of the invention comprising a restriction device having an elongated restriction member in the form of a circular resilient core 2 with two overlapping end portions 4,6. The core 2 defines a substantially circular restriction opening and is enclosed in an elastic soft hose 8 except at a releasable and lockable joint 10 of the core 2, which when released enables application of the core 2 with its hose 8 around a tissue of a patient, such as the colon or rectum or one or more exit rectum from the patient's colon or rectum. The materials of all of these elements are bio-compatible so that the patient' body will not reject them. A mechanical adjustment device 12 for mechanically adjusting the longitudinal extension of the core 2 to change the size of the restriction opening comprises a drive wheel 14 in frictional engagement with the overlapping end portions 4,6 of the core 2. The drive wheel 14 is journalled on a holder 16 placed in the hose 8 and provided with two counter pressure rollers 18,20 pressing the respective end portions 4, 6 of the core 2 against the drive wheel 14 to increase the frictional engagement there between. An electric motor 22 is connected to the drive wheel 14 via a long flexible drive shaft 24 and is moulded together with a remote controlled power supply unit 26 in a body 28 of silicone rubber. The length of the flexible drive shaft 34 is selected so that the body 28 can be placed in a desired position in the patient_s body, suitably in the abdomen.

When the patient doesn't want to relieve himself (defaecation), he controls the power supply unit 26 to power the electric motor 22 to turn the drive wheel 14 in one direction to reduce the diameter of the core 2, so that the tissue is squeezed and the fecal passageway is restricted. When the patient wishes to relieve himself he controls the power supply unit 26 to power the electric motor 22 to turn the drive wheel 14 in the opposite direction to increase the diameter of the core 2, so that the fecal passageway is open.

Alternatively, a rack gear may be formed on one of the end portions 4,6 of the core 2 and the drive wheel 14 may be replaced by a drive gear wheel connected to the other end portion of the core 2 and in mesh with the rack gear.

FIG. 4 shows an embodiment of the invention which is identical to the embodiment of FIGS. 1-3, except that the motor 22 is encapsulated in a lateral protrusion 30 of the hose 8 so that it is fixed to the core 2 and has a short drive shaft 32 onto which the drive wheel 14 is mounted, and that the motor 22 is positioned relative to the circular core 2 such that the drive shaft 32 extends radially thereto.

FIG. 5 shows an embodiment of the invention which likewise is identical to the embodiment of FIGS. 1-3, except that the motor 22 is encapsulated in the hose 8 so that it is fixed to the core 2 and has a short drive shaft 32, and that the motor 22 is positioned relative to the core 2 such that the drive shaft 32 extends substantially tangentially to the circular core 2. There is an angular gearing 34 connecting the drive shaft 32 to the drive wheel 14.

FIG. 6 shows a suitable arrangement for the motor 22 in the embodiment of FIG. 5, comprising a first clamping member 36 secured to one end portion of the core 2 and a second clamping member 38 secured to the other end portion 6 of the core 2. The motor 22 is secured to the first clamping member 36 and is operatively connected to a worm 40 via a gear transmission 42. The worm 40 is journalled at its opposite ends on holders 44 and 46, which are rigidly secured to the clamping member 36 and the motor 22, respectively. The second clamping member 38 has a pinion in mesh with the worm 40. When the motor 22 is powered the worm 40 rotates and will thereby pull the end portion 6 of the core 2 in one or the opposite longitudinal direction, so that the diameter of the substantially circular core 2 is either increased or decreased.

FIG. 7 shows an embodiment of the invention in which the elongated restriction member comprises a core 48 and a helical spring 50. A spring contracting means in the form of a flexible pulling member 52, i.e. a string, wire or cable, is connected to the core 48 at one end thereof and extends through the helical spring 50. A hydraulic motor in the form of a cylinder/piston unit 54 is adapted to pull the flexible pulling member 52 to contract the helical spring 50 against an arresting member 56, which is fixed relative to the core 48. A tube 58 hinged to the arresting member 56 extends between the cylinder/piston unit 54 and the arresting member 56, the flexible pulling member 52 running through the tube 58 and being connected to the piston of the cylinder/piston unit 54. FIG. 8 shows a similar embodiment in which a hydraulic transmission conduit 59 is provided between two piston-cylinder assemblies 54, for use as the hydraulic motor/device in FIG. 7.

FIG. 9 shows an embodiment of the invention in which the restriction member comprises two elongated helical springs 60 and 62 having free ends, and a body 64 to which the springs 60,62 are nonrotatably secured at their opposite ends. The body 64 comprises two separate parts secured to opposite end portions of the enclosing elastic hose 8 and is designed with a releasable and lockable joint between the separate parts. An adjustment device in the form of a drive shaft 66 has two opposite end portions connected to the helical springs 60,62, respectively, at their free ends. The coils of the springs 60,62 form left and right hand helices, respectively. A motor 68 is adapted to rotate the drive shaft 66 in one direction to enlarge the coils of the helical springs 60,62 to longitudinally contract the springs 60,62 and to rotate the drive shaft 66 in the opposite direction to reduce the size of the coils of the springs 60,62 to longitudinally extend the springs 60,62. Thus, the elongated helical springs 60,62 defines a restriction opening, the size of which is increased when the springs 60,62 are extended and decreased when the springs 60,62 are contracted.

FIG. 10 shows an embodiment according to the invention which is identical to the embodiment of FIG. 9, except that the adjustment device comprises a gearing having an input shaft 72 and two opposite aligned output shafts 74 and 76 connected to the helical springs 60 and 62, respectively, at their free ends. The input shaft 72 is connected to the output shafts 74,76 such that they rotate at opposite directions upon rotation of the input shaft 72. The coils of the springs 60, 62 form the same helices.

FIGS. 11-14 show an embodiment of the device of the invention in which a hydraulic motor comprises two interconnected cylinders 78 and 80 and two pistons 82 and 84 in the respective cylinders 78,80. The cylinders 78,80 have a common fluid supply inlet member 86, which together with the cylinders 78,80 takes the shape of a Y-pipe. The restriction member comprises an elongated resilient arcuate core 88. The adjustment device comprises two bars 90 and 92 secured to opposite ends of the core 88 and connected to the pistons 82 and 84, respectively. The core 88 defines a restriction opening and is provided with a releasable and lockable joint 94 (FIG. 13) to permit application of the core 88 around the tissue. The core 88 and the cylinders 90,92 are enclosed by a soft elastic hose 96 except at the joint 94 and the inlet member 86. The hose 96 has an outer tubular wall 98 and a central coaxial inner tubular wall 100, which is fixed to the outer wall 98 by spoke members 102 (FIG. 14). The core 88 is loosely fit in the inner tubular wall 100. By supplying fluid to or withdrawing fluid from the inlet 86 the pistons 82 and 84 will move towards or from each other, so that the restriction opening defined by the core 88 is changed by the longitudinal displacement of the bars 90,92.

FIGS. 15-17 show an embodiment of the invention which is identical to the embodiment of FIGS. 11-14, except that the adjustment device comprises an elongated voltage responsive element 104 secured to the opposite ends of the core 88, so that the core 88 and the element 104 form the restriction member. The element 104 is capable of bending inwardly into a bow in response to a voltage applied across the element 104. The radius of curvature of said bow is adjustable by changing the level of the voltage applied to element 104.

FIG. 18 shows an embodiment of the invention comprising a loop forming means in the form of a substantially rigid outer circular element 106 with a releasable and lockable joint 108. In this embodiment the restriction member comprises an elastic inner circular element 110 formed by the innermost wall portion of an elastic hose 112 extending along the outer element 106. The inner circular element 110 is disposed concentrically within the outer circular element 106. The adjustment device comprises a plurality of threads 114 secured to the elastic inner element 110 along the circumference thereof and running from the inner element 110 via guide members 116 attached to the outer element 106. By pulling all the threads 114 the inner elastic element 110 is pulled under expansion radially outwardly towards the outer element 106.

FIG. 19 shows an embodiment which is identical to the embodiment of FIG. 9, except that it comprises a loop forming means in the form of a substantially rigid outer circular element 118 supporting the helical springs 60,62, and a soft elastic inner wall 120 extending along the springs 60,62. When the motor 68 rotates the helical springs 60, 62 in a direction that enlarges the coils of the springs 60,62, the coils are forced by the rigid outer element 118 to expand radially inwardly thereby reducing the size of the restriction opening formed by the circumferential confinement surface of the restriction member (springs 60,62 and body 64).

FIG. 20 shows an embodiment of the invention in which a restriction member comprises a plurality of arcuate lamellae 122 arranged like the conventional adjustable aperture mechanism of a camera. The adjustment device, not shown, is conventional and is operated by a motor 124 to adjust the lamellae 122 to change the size of an restriction opening defined by the lamellae 122.

FIGS. 21-23 show an embodiment of the invention in which a restriction member comprises two semi-circular elements 126 and 128 which are hinged together such that the semi-circular elements 126,128 are swingable relative to each other between a fully open state in which they substantially form a circle, illustrated in FIG. 22 and an angular state, in which the size of the restriction opening defined by the semi-circular elements 126,128 is reduced, illustrated in FIG. 23. The adjustment device, not shown, is conventional and is operated by a motor 130 to swing the semi-circular elements 126,128 relative to each other.

FIGS. 24-27 show an embodiment of the invention in which a restriction member comprises an elastic belt 130 forming a circle and having a substantially oval cross-section. The restriction member 130 is provided with a releasable and lockable joint 132. An elastic double walled hose 134 encloses the belt 130 except at the joint 132. The adjustment device, not shown, is conventional and is operated by a motor 136 to turn the belt 130 around the longitudinal extension thereof between a fully open state, in which the inner broader side of the belt 130 forms a substantially cylindrical surface, illustrated in FIG. 26, and a reduced open state, in which the inner broader side of the belt 130 forms a substantially conical surface, illustrated in FIG. 27.

FIG. 28 schematically illustrates a cushion arrangement for protecting the tissue, comprising a plurality of cushions 138 disposed in series along a substantially circular holding member 140. This cushion arrangement may be utilized in any of the above described embodiments of the invention.

Figure 29A:
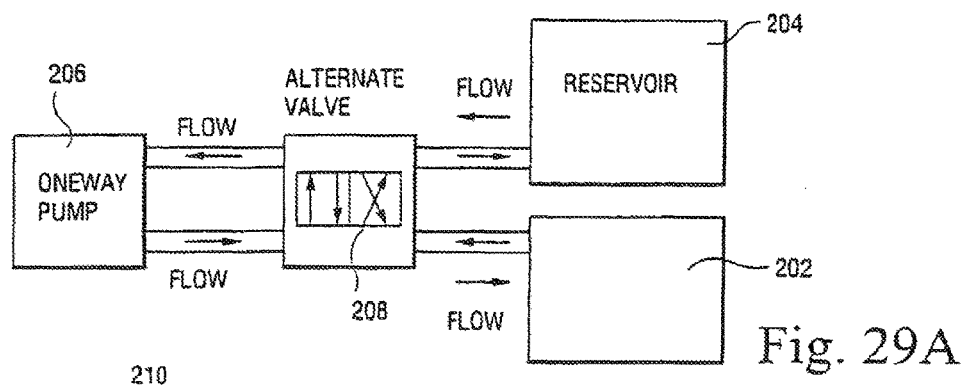
FIG. 29A-D is a block diagram of four different principal embodiments of the invention.
Figure 29B:
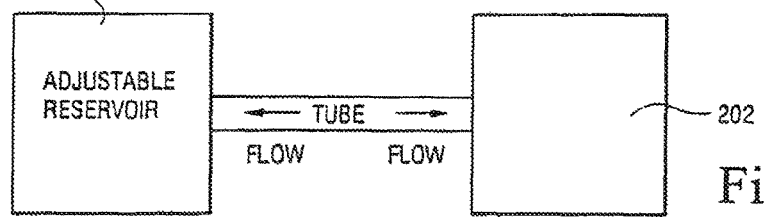
Figure 29C:
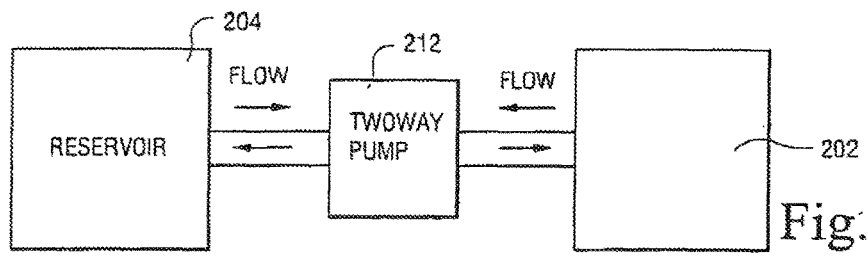

FIGS. 29A-D provide a block diagram of four different hydraulic transmission configurations. FIG. 29A shows an adjustment device 202, a separate reservoir 204, a one way pump 206 and an alternate valve 208. FIG. 29B shows the adjustment device 202 and an adjustable reservoir 210. FIG. 29C shows the adjustment device 202, a two way pump 212 and the reservoir 204. FIG. 30D shows a servo system with a first closed system controlling a second system. The servo system comprises the adjustable reservoir 210 and a passive adjustable reservoir 214. Any of the reservoirs can be the active reservoir, either the servo reservoir 210 or the fluid supply reservoir 214. The reservoir 214 controls a larger adjustable reservoir 216 which is used for the operation of the adjustment device 202 for changing the restriction opening of the restriction member.

Figure 30A:
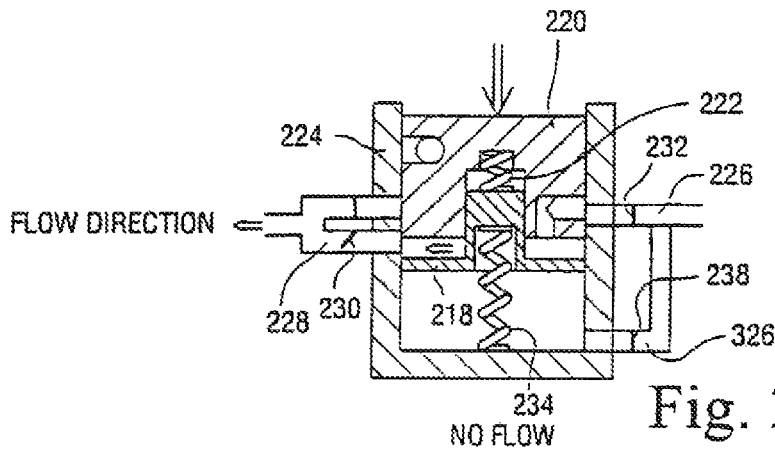
FIG. 30A-D are cross-sectional views of a pump mechanism according to FIG. 29C, which pumps fluid in opposite directions by mechanically pushing a wall portion in only one direction.
Figure 30B:
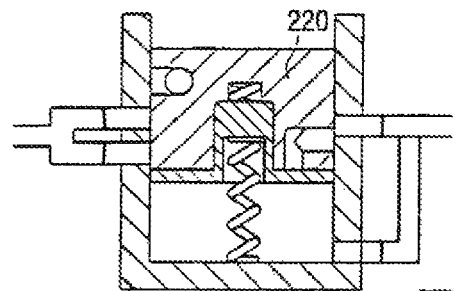
Figure 30C:
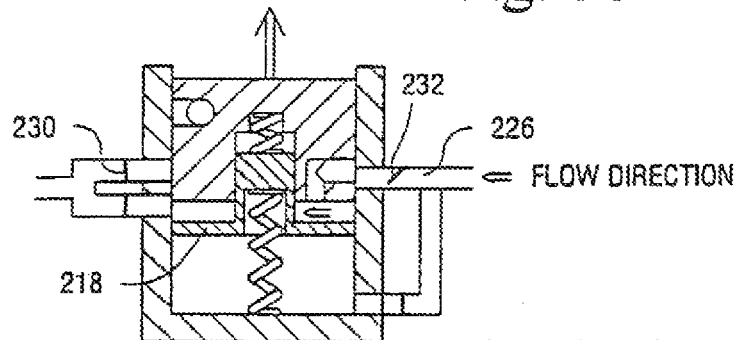

FIGS. 30A-D are cross-sectional views of a pump mechanism adapted to pump fluid in both directions only by mechanically pushing a separate sealing wall portion 218 in one direction. FIG. 30A shows a piston 220 pushed forwards against a spring 222 towards the wall portion 218 and located in a pump housing 224 conducting fluid from a right upper fluid passage 226 of the housing 224 to a left fluid passage 228 of the housing 224. A main valve 230 is open and a nonreturn valve 232 is closed. FIG. 30B illustrates the first pump movement in which the piston 220 has moved forwards and reaches the wall portion 218. FIG. 30C illustrates how the piston 220 moves backwards by the action of the spring 222. The main valve 230 is now closed and the nonreturn valve 232 is open for fluid from the right upper passage 226. FIG. 30D illustrates how the piston 220 is moved further downwards from its position according to FIG. 30B while pushing the wall portion 218 downwards against a second spring 234 that is stronger than spring 222, so that fluid escapes from a right lower fluid passage 236. When moving the piston 220 backwards from the position of FIG. 30D, fluid enters the left fluid passage 228 and a valve 238 in the lower right fluid passage 236 closes.

Figure 29D:
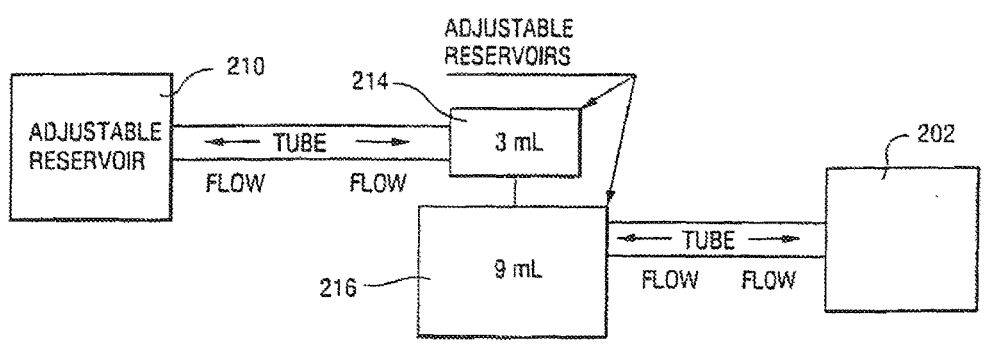
Figure 30D:
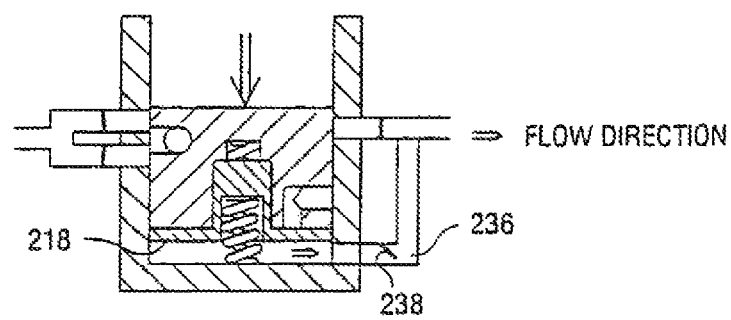
Figure 31:
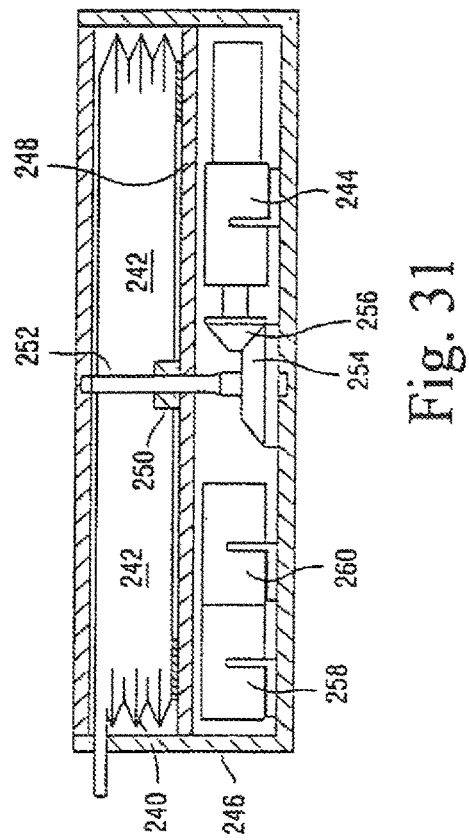
FIG. 31 is a cross-sectional view of a reservoir having a variable volume controlled by a remote control motor, in accordance with a particular embodiment of the principal embodiment shown in FIG. 29B or 30B.

FIG. 31 is a cross-sectional view of a reservoir 240 defining a chamber 242, the size of which is variable and is controlled by a remote controlled motor 244, in accordance with FIG. 29B or 29D. The reservoir 240 and the motor 244 are placed in a housing 246. The chamber 242 is varied by moving a large wall 248. The wall 248 is secured to a nut 250, which is threaded on a rotatable spindle 252. The spindle 252 is rotated by the motor 244 via an angular gearing, which comprises two conical gear wheels 254 and 256 in mesh with each other. The motor 244 is powered by a battery 258 placed in the housing 246. A signal receiver 260 for controlling the motor 244 is also placed in the housing 246. Alternatively, the battery 258 and the signal receiver 260 may be mounted in a separate place. The signal receiver may comprise any known or conventional device which is capable of receiving a control signal and then operating the motor 244.

Figure 32:
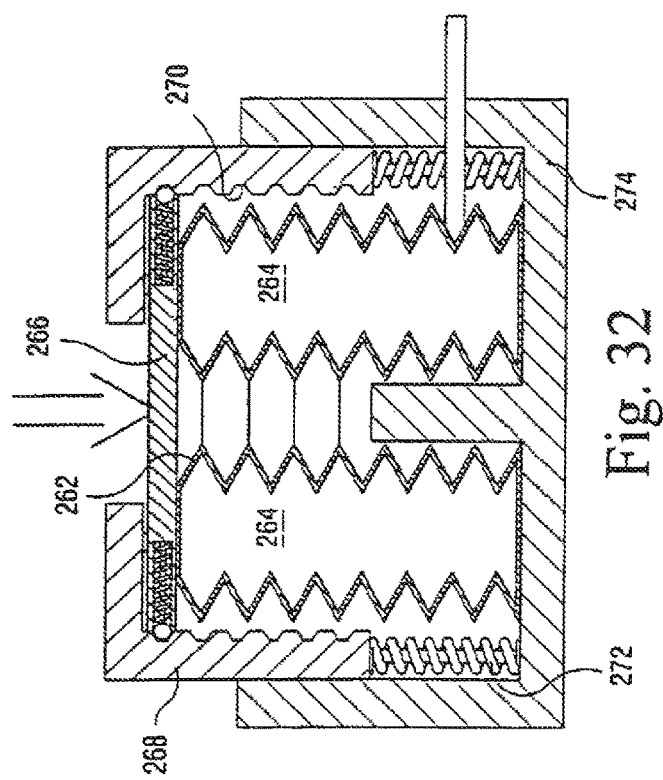
FIG. 32 is a cross-sectional view of a reservoir having a variable volume adjustable by manual manipulation, in accordance with a particular embodiment of the principal embodiment shown in FIG. 29B or 29D.

FIG. 32 is a cross-sectional view of a reservoir 262 defining a chamber 264, the size of which is variable and is controlled by manual manipulation. A gable wall portion 266 of an open ended inner cylindrical housing 68 is adapted to be pushed downwards to fit in a desired locking groove 270 of a plurality of locking grooves 270 on the mantle wall of the cylindrical housing 268, to reduce the size of the chamber 64. The inner cylindrical housing 268 is suspended by springs 272 and is telescopically applied on an outer cylindrical housing 274. When pushing the inner cylindrical housing 268 it moves downwards relative to the outer cylindrical housing 274 causing the gable wall portion 266 to release from the locking groove 270 and move upwards relative to the inner cylindrical housing 268. When the inner housing 268 is moved upwardly by the action of the springs 272 the size of the chamber 264 is increased.

FIGS. 33A and 33B show a servo means comprising a main ring-shaped fluid reservoir 276 defining a chamber 278, the size of which is variable. Centrally positioned in the main ring-shaped reservoir 276 there is a servo fluid reservoir 280 defining a chamber 282, the size of which is variable. The chamber 282 of the servo reservoir 280 is significantly smaller than the chamber 278 of the main reservoir 276. The two reservoirs 276 and 280 are situated between two opposite separate walls 284 and 286, and are secured thereto. When changing the amount of fluid in the servo reservoir 280, the two opposite walls 284,286 are moved towards or away from each other, whereby the size of the chamber 278 of the main reservoir 276 is changed.

Figure 34:
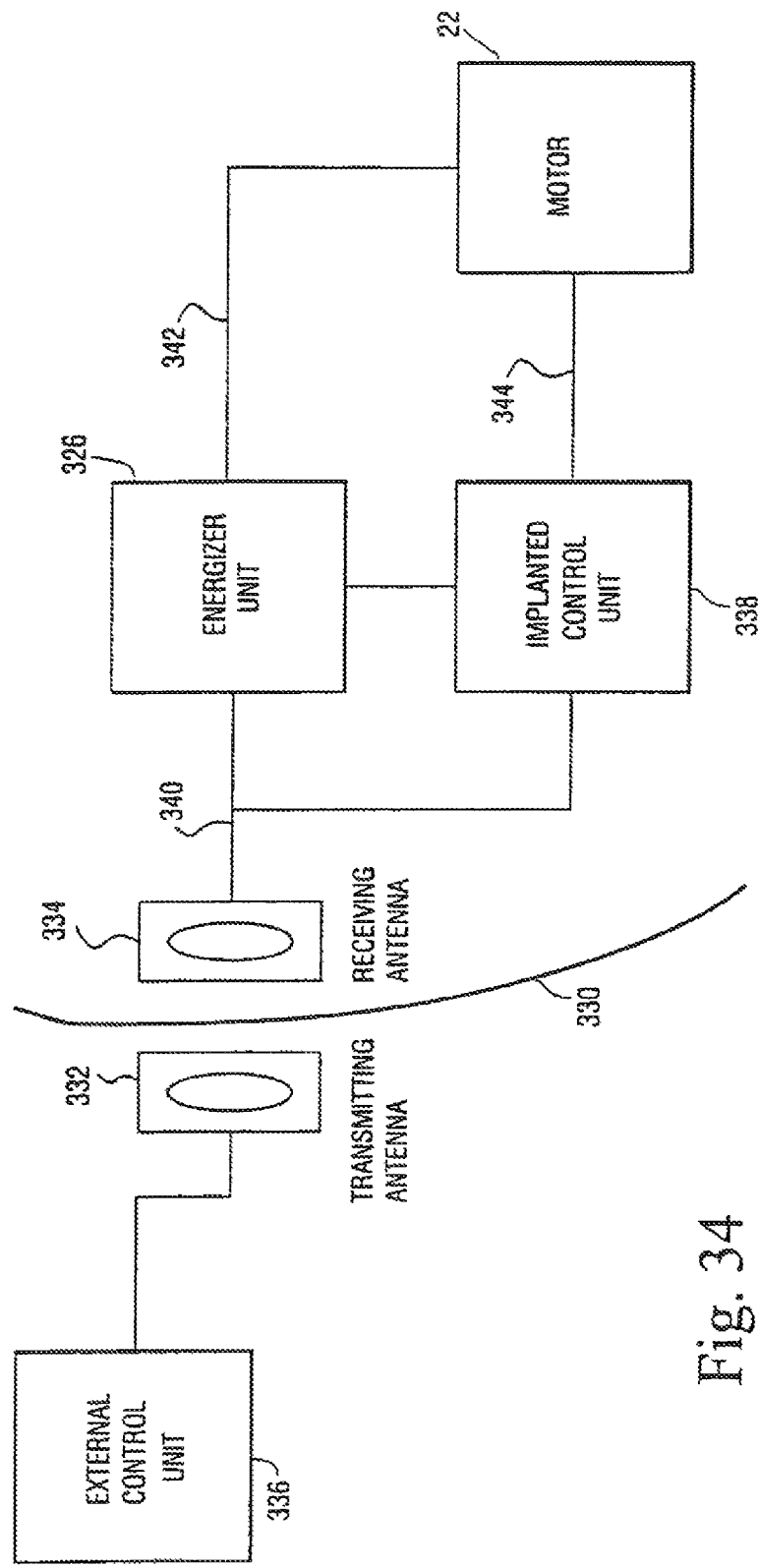
FIG. 34 is a block diagram illustrating remote control components of the apparatus of the invention.

FIG. 34 shows the basic parts of a remote control system of the apparatus of the invention including a motor, for instance the electric motor 22. In this case, the remote control system is based on the transmission of an electromagnetic wave signal, often of a high frequency in the order of 100 kHz-1 gHz, through the skin 330 of the patient. In FIG. 34, all parts placed to the left of the skin 330 are located outside the patient_s body and all parts placed to the right of the skin 330 are implanted in the patient_s body.

An external signal transmitting antenna 332 is to be positioned close to a signal receiving antenna 334 implanted in the patient_s body close to the skin 330. As an alternative, the receiving antenna 334 may be placed for example inside the abdomen of the patient. The receiving antenna 334 comprises a coil, approximately 1-100 mm, preferably 25 mm in diameter, wound with a very thin wire and tuned with a capacitor to a specific high frequency. A small coil is chosen if it is to be implanted under the skin of the patient and a large coil is chosen if it is to be implanted in the abdomen of the patient. The transmitting antenna 332 comprises a coil having about the same size as the coil of the receiving antenna 334 but wound with a thick wire that can handle the larger currents that is necessary. The coil of the transmitting antenna 332 is tuned to the same specific high frequency as the coil of the receiving antenna 334.

An external control unit 336 comprises a microprocessor, a high frequency electromagnetic signal generator and a power amplifier. The microprocessor of the control unit 336 is adapted to switch on/off the generator and to modulate signals generated by the generator to send digital information via the power amplifier and the antennas 332,334 to an implanted control unit 338. To avoid that accidental random high frequency fields trigger control commands, digital signal codes are used. A keypad placed on the external control unit 336 is connected to the microprocessor thereof. The keypad is used to order the microprocessor to send a digital signal to either increase or decrease the size of the restriction opening defined by the loop of the restriction member (e.g. as described above). The microprocessor starts a command by applying a high frequency signal on the antenna 332. After a short time, when the signal has energized the implanted parts of the control system, commands are sent to increase or decrease the size of the restriction opening of the restriction member in predefined steps. The commands are sent as digital packets in the form illustrated below.

| Start pattern, 8 bits | Command, 8 bits | Count, 8 bits | Checksum, 8 bits |
|---|---|---|---|

The commands are sent continuously during a rather long time period (e.g. 30 seconds or more). When a new increase or decrease step is desired the Count byte is increased by one to allow the implanted control unit 338 to decode and understand that another step is demanded by the external control unit 336. If any part of the digital packet is erroneous, its content is simply ignored.

Through a line 340, an implanted energizer unit 326 draws energy from the high frequency electromagnetic wave signal received by the receiving antenna 334. The energizer unit 326 stores the energy in a power supply, such as a large capacitor, powers the control unit 338 and powers the electric motor 22 via a line 342.

The control unit 338 comprises a demodulator and a microprocessor. The demodulator demodulates digital signals sent from the external control unit 336. The microprocessor of the control unit 338 receives the digital packet, decodes it and, provided that the power supply of the energizer unit 326 has sufficient energy stored, sends a signal via a signal line 344 to the motor 22 to either increase or decrease the size of the restriction opening of the restriction member depending on the received command code.

Alternatively, the energy stored in the power supply of the energizer unit may only be used for powering a switch, and the energy for powering the motor 22 may be obtained from another implanted power source of relatively high capacity, for example a battery. In this case the switch is adapted to connect the battery to the control unit 338 in an _on_ mode when said switch is powered by said power supply and to keep said battery disconnected from the control unit in a _standby_ mode when the switch is unpowered.

Figure 35:
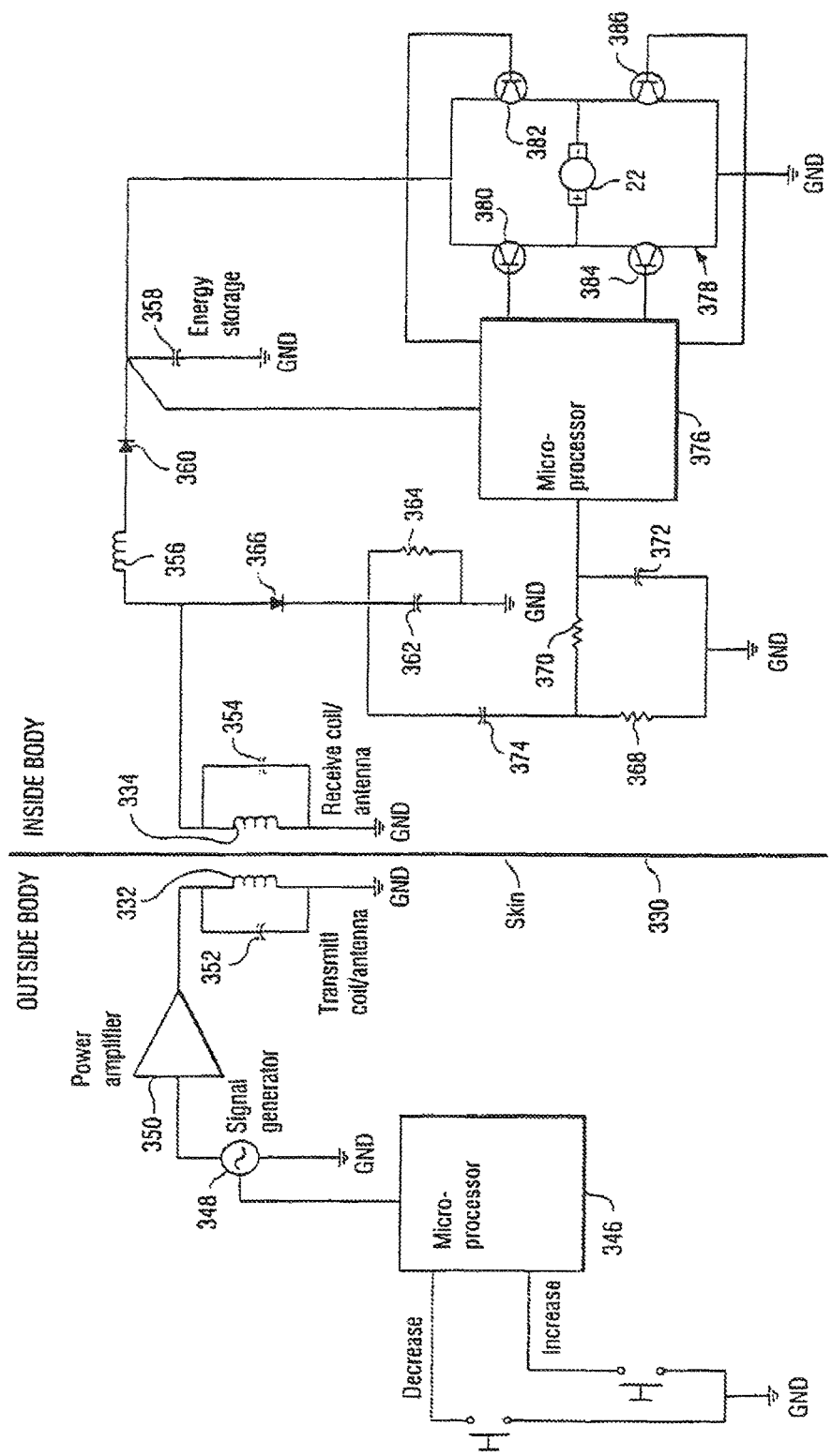
FIG. 35 is a schematic view of a circuitry used for the system of the block diagram of FIG. 34.

With reference to FIG. 35, the remote control system schematically described above will now be described in accordance with a more detailed embodiment. The external control unit 336 comprises a microprocessor 346, a signal generator 348 and a power amplifier 350 connected thereto. The microprocessor 346 is adapted to switch the signal generator 348 on/off and to modulate signals generated by the signal generator 348 with digital commands that are sent to implanted components of the device of the invention. The power amplifier 350 amplifies the signals and sends them to the external signal transmitting antenna 332. The antenna 332 is connected in parallel with a capacitor 352 to form a resonant circuit tuned to the frequency generated by the signal generator 348.

The implanted signal receiving antenna coil 334 forms together with a capacitor 354 a resonant circuit that is tuned to the same frequency as the transmitting antenna 332. The signal receiving antenna coil 334 induces a current from the received high frequency electromagnetic waves and a rectifying diode 360 rectifies the induced current, which charges a storage capacitor 358. A coil 356 connected between the antenna coil 334 and the diode 360 prevents the capacitor 358 and the diode 360 from loading the circuit of the signal receiving antenna 334 at higher frequencies. Thus, the coil 356 makes it possible to charge the capacitor 358 and to transmit digital information using amplitude modulation.

A capacitor 362 and a resistor 364 connected in parallel and a diode 366 forms a detector used to detect amplitude modulated digital information. A filter circuit is formed by a resistor 368 connected in series with a resistor 370 connected in series with a capacitor 372 connected in series with the resistor 368 via ground, and a capacitor 374, one terminal of which is connected between the resistors 368, 370 and the other terminal of which is connected between the diode 366 and the circuit formed by the capacitor 362 and resistor 364. The filter circuit is used to filter out undesired low and high frequencies. The detected and filtered signals are fed to an implanted microprocessor 376 that decodes the digital information and controls the motor 22 via an H-bridge 378 comprising transistors 380,382,384 and 386. The motor 22 can be driven in two opposite directions by the H-bridge 378.

The microprocessor 376 also monitors the amount of stored energy in the storage capacitor 358. Before sending signals to activate the motor 22, the microprocessor 376 checks whether the energy stored in the storage capacitor 358 is enough. If the stored energy is not enough to perform the requested operation, the microprocessor 376 waits for the received signals to charge the storage capacitor 358 before activating the motor 22.

FIGS. 36A and 36B show an embodiment of the apparatus of the invention comprising a restriction device 402 having an elongated flexible restriction member 404, such as a belt, a cord or the like. The flexible member 404 extends in a loop around the tissue, suitably the rectum or colon or its prolongation. (Alternatively, the flexible member 404 may comprise two separate parts on opposite sides of the colon or rectum or the prolongation thereof) One portion 404A of member 404 is attached to a frame 408 and another portion 404B of member 404 opposite portion 404A in the loop of the flexible member 404 is connected to an adjustment device 410, which is fixed to the frame 408. The adjustment device 410 pulls the flexible member 404 in the direction from portion 404A to squeeze the colon or rectum or the prolongation thereof between two opposite lengths of the flexible member 404 to thereby restrict the fecal passageway in the colon or rectum or the prolongation thereof 406, see FIG. 36A, and releases the colon or rectum or the prolongation thereof from the flexible member 404 to thereby increase the fecal passageway to allow defaecation 406, see FIG. 36B.

FIGS. 37A and 37B show an embodiment of the apparatus of the invention comprising a restriction device 412 having two plate or bar elements 414 on opposite sides of the rectum 406. An adjustment device 416 moves the elements 412 in parallel towards each other to squeeze the rectum 406 between the elements 412 to thereby restrict the blood flow in the rectum 406, see FIG. 37A, and moves the elements 412 away from each other to release the rectum 406, see FIG. 37B.

FIG. 38 shows an embodiment of the apparatus of the invention comprising a restriction device 418 having two rigid articulated clamping elements 420 positioned on opposite sides of the rectum 406. An adjustment device 422 turns the clamping elements 420 toward each other to clamp the rectum 406 between the clamping elements 420 to thereby restrict the fecal passageway in the rectum 406, and turns the clamping elements 420 away from each other to release the rectum 406 from the clamping elements 420 to thereby increase the restriction of the fecal passageway to allow defaecation.

FIGS. 39A, 39B and 39C show an embodiment of the apparatus of the invention comprising a restriction device 424 having three bending members in the form of cylindrical rollers 426, 428 and 430 displaced relative one another in a row along the rectum 406 and positioned alternately on opposite sides of the rectum 406. (Alternatively, each roller 426, 428 and 430 may take the shape of an hour-glass.) An adjustment device 432 moves the two outer rollers 426,430 laterally against the rectum 406 in one direction and the intermediate roller 428 against the rectum 406 in the opposite direction to bend the rectum to thereby restrict the fecal passageway in the rectum 406, see FIG. 39B. To increase the fecal passageway to allow defaecation 406, the adjustment device 432 moves the rollers 426-430 away from the rectum 406 to release the latter from the rollers 426-430, see FIG. 39C.

Figure 40A:
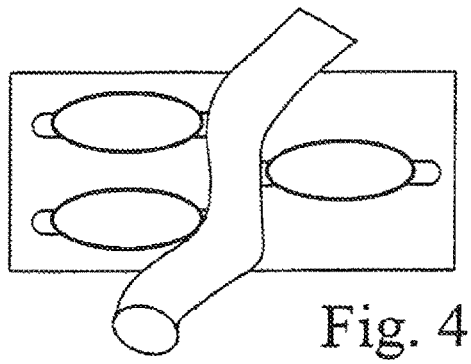
FIGS. 40A through 44B are five modifications of the embodiment of FIGS. 39A-39C.
Figure 40B:
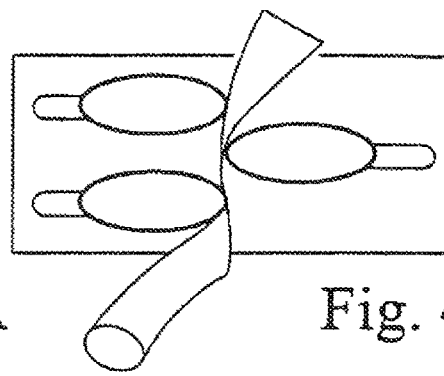
Figure 41A:
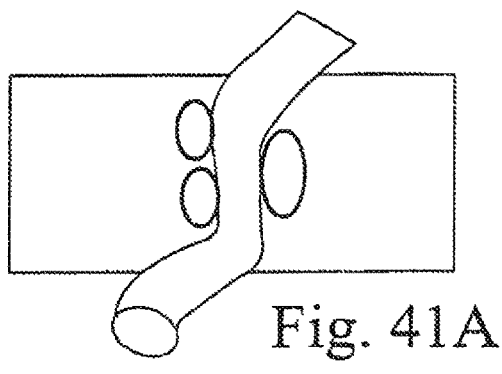
Figure 41B:
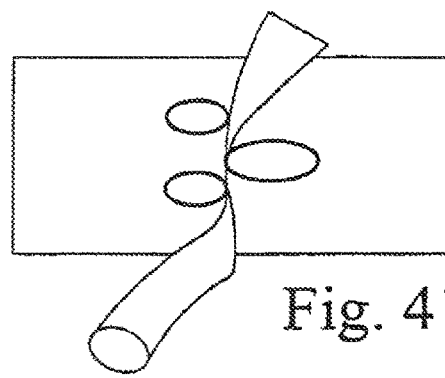
Figure 42A:
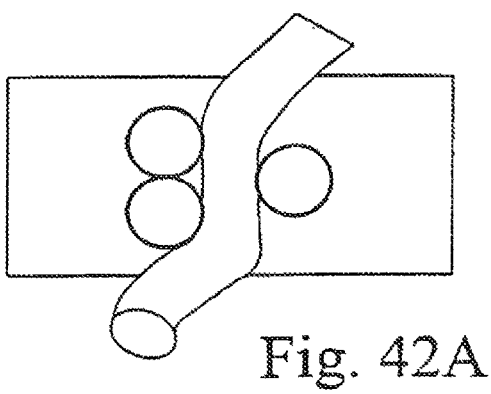
Figure 42B:
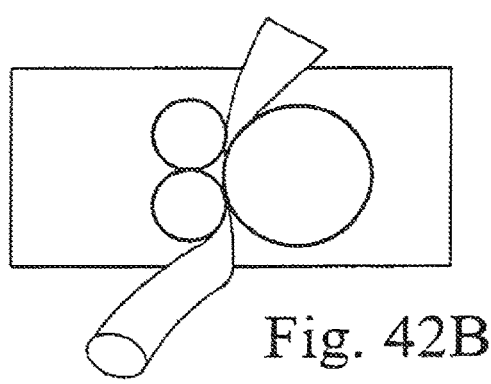
Figure 43A:
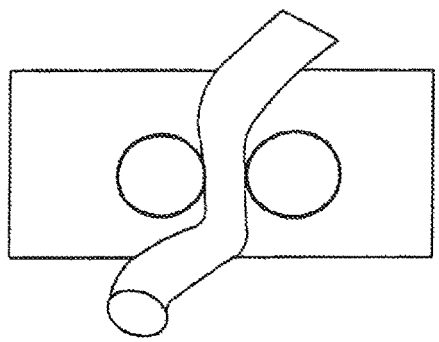
Figure 43B:
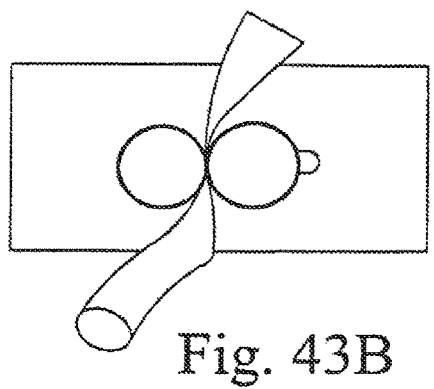
Figure 44A:
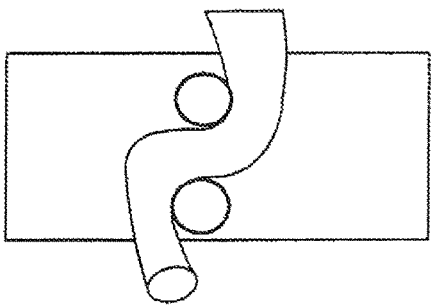
Figure 44B:
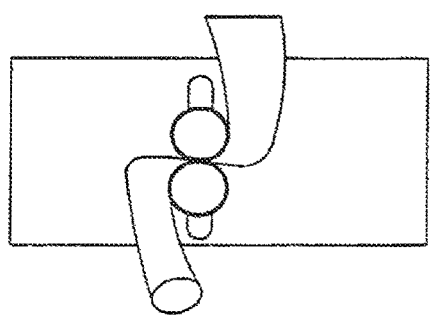

FIGS. 40A through 44B schematically illustrates modifications of the above embodiment according to FIGS. 39A-39C. Thus, FIGS. 40A and 40B show an embodiment similar to that of FIGS. 39A-39C except that the bending members are oval and not rotatable. FIGS. 41A and 41B show an embodiment similar to that of FIGS. 40A and 40B except that the oval bending members are rotatable to release the rectum, see FIG. 41A, and squeeze the rectum, see FIG. 41B. FIGS. 42A and 42B show an embodiment similar to that of FIGS. 39A-39C except that the intermediate roller has a changeable diameter to release the rectum, see FIG. 42A, and squeeze the rectum, see FIG. 42B. FIGS. 43A and 43B show an embodiment similar to that of FIGS. 37A-37C except that the rigid elements are replaced by two cylindrical rollers positioned on opposite sides of the rectum. Finally, FIGS. 44A and 44B show an embodiment substantially similar to that of FIGS. 43A and 43B except that the restriction device is curved to form an S-shaped curvature of the rectum.

Figure 45:
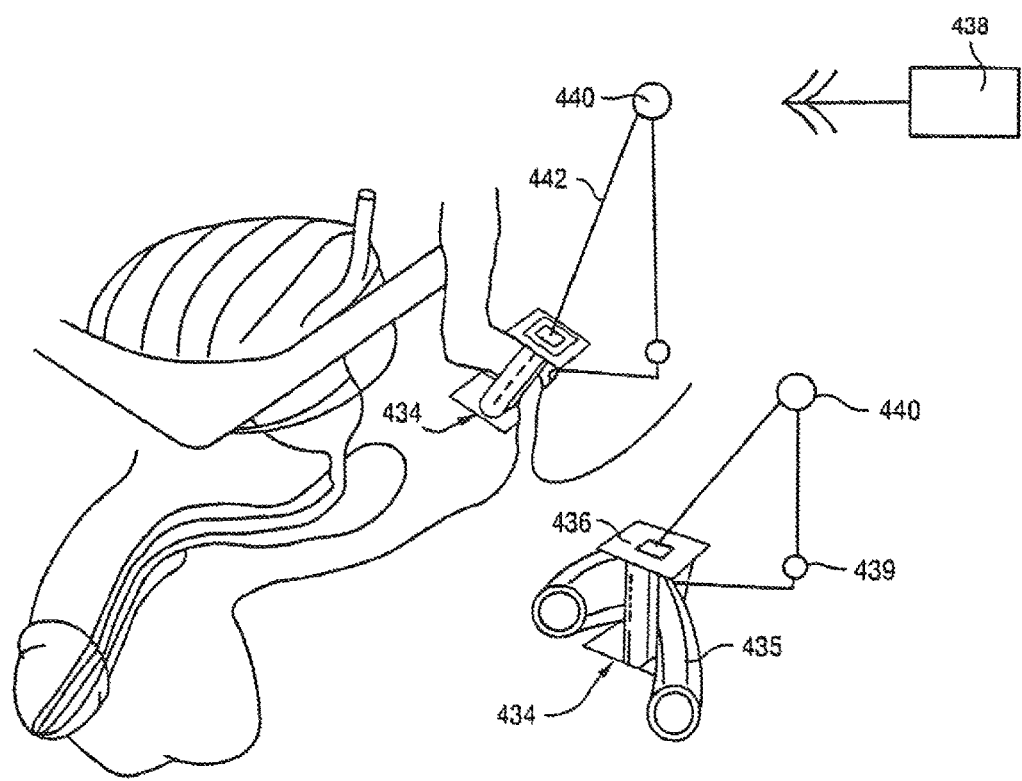
FIG. 45 illustrates the apparatus of the invention with a restriction device implanted around the colon.

FIG. 45 schematically illustrates how any of the above-described embodiments of the anal incontinence treatment apparatus of the invention may be implanted in a patient. Thus, the apparatus comprises an adjustable restriction device 434 extending around the rectum 435 of the patient and a motor operated adjustment device 436 for mechanically adjusting the restriction device 434 to squeeze rectum to thereby restrict the fecal passageway in the rectum. The motor, not shown, is integrated in the adjustment device 436 and is reversible to operate the adjustment device 436 to release the rectum from the restriction device 434 to allow defaecation. A wireless remote control of the apparatus comprises an external signal transmitter 438 incorporated in a portable remote-control unit and an implanted signal receiver 440, which comprises a control unit for controlling the adjustment device 436 in response to a control signal, for example an electromagnetic wave signal, from the transmitter 438. The signal receiver 440 further comprises an energizer unit which transfers energy from the control signal transmitted by the transmitter 438 into electric energy for energy consuming implanted components of the apparatus, such as the motor for operating the adjustment device 436. The electric energy is conducted via an implanted conductor 442 from the signal receiver 440 to the motor. When the patient needs to relieve himself (defaecation), he readily uses the portable remote control unit to activate the implanted adjustment device 436 to temporarily adjust the implanted restriction device 434 to start release the fecal passageway to allow defaecation.

A pressure sensor 439 is implanted for sensing the pressure on the restriction device 434. The control unit of the signal receiver 449 controls the adjustment device 436 to release the restriction device 434 in response to the pressure sensor 439 sensing an abnormal high pressure.

In the practice of the present invention the details of the elongated restriction device (such as a gastric band) and the adjustment/operation device (which may have electric, hydraulic, or mechanical, etc. actuation), may be as described in copending application Ser. No. 09/133,319, filed Aug. 13, 1998, Ser. No. 09/133,320, filed Aug. 13, 1998 and Ser. No. 09/133,322, filed Aug. 13, 1998, the disclosures of which are incorporated by reference herein.

There are a number of other conceivable alternative embodiments of the invention that give the same result as the above-described embodiments. For example, the microprocessor of the external and implanted, respectively, control unit may be replaced by discrete components. The power amplifier of the external control unit may be omitted if the signals generated by the signal generator are strong enough. Therefore the invention is to be accorded the broadest interpretation of the appended claims to encompass all equivalent structures and assemblies.

I claim:

1. An anal incontinence treatment apparatus, comprising:
   an adjustable non-inflatable restriction device adapted to be implanted in a patient, who suffers from anal incontinence, to restrict a fecal passageway of the patient,
   a hydraulic adjustment device adapted to be implanted in the patient for adjusting said restriction device to restrict the fecal passageway to prevent feces from passing therethrough and to enlarge the fecal passageway to allow feces to readily pass therethrough,
   an implantable reservoir adapted to contain a predetermined amount of hydraulic fluid, providing a fluid connection between said reservoir and said hydraulic adjustment device,
   a powered operation device adapted to be implanted in the patient for operating said hydraulic adjustment device by distributing hydraulic fluid between said reservoir and said hydraulic adjustment device, and
   a control device adapted to be noninvasively controlled from outside a body of the patient comprising
      a first implantable control unit for controlling both a constriction and release of the adjustable restriction device to open and close the fecal passageway, and
      a second control unit adapted to send a control signal to the first control unit, operated from outside the patients body.

2. The apparatus according to claim 1, wherein the operation device includes a servo operatively connected to the hydraulic adjustment device, wherein the servo includes a mechanism that transfers a weak force acting on a moving element having a long stroke into a strong force acting on another moving element having a short stroke.

3. The apparatus according to claim 1, wherein the restriction device is adapted to reversibly and steplessly control a cross-sectional area of the fecal passageway.

4. The apparatus according to claim 1, wherein the restriction device comprises at least one of:
   an element to be placed on one side of a portion of the fecal passageway, wherein the adjustment device is adapted to squeeze said portion between the element and a human bone or tissue to restrict the faecal passageway, and
   at least two elements to be placed on different sides of said portion of the fecal passageway, wherein the hydraulic adjustment device is adapted to squeeze said portion between the elements to restrict the faecal passageway in said portion, and to release said portion of the fecal passageway to allow enlargement of the fecal passageway.

5. The apparatus according to claim 1, wherein the restriction device comprises at least one elongated restriction member and forming means for forming the restriction member into a partial or fully closed loop around a portion of the fecal passageway, the partial or fully closed loop defining a restriction opening, whereby the adjustment device is adapted to adjust the restriction device in the partial or fully closed loop to change a size of the restriction opening.

6. The apparatus according to claim 5, wherein the restriction device comprises several of the elongated restriction members to be formed into several of the partial or fully closed loops around the fecal passageway.

7. The apparatus according to claim 5, wherein the hydraulic adjustment device is adapted to change a size of the restriction opening such that an outer circumferential confinement surface of the restriction device is changed.

8. The apparatus according to claim 1, wherein the restriction device comprises at least two bending members adapted to be positioned on opposite or different sides of a portion of the fecal passageway and to be displaced relative to each other along the fecal passageway in said portion, and wherein the hydraulic adjustment device is adapted to move the bending members against said portion of the fecal passageway to bend it to restrict the faecal passageway, and to move the bending members away from said portion to release it from the bending members to allow enlargement of the faecal passageway.

9. The apparatus according to claim 1, wherein the operation device comprises a pump, a motor, or a pump and a motor adapted to pump fluid between the reservoir and the restriction device.

10. The apparatus according to claim 9, further comprising an external energy transmitter for transmitting wireless energy wherein the wireless energy comprises a magnetic field or electromagnetic waves adapted to directly power the motor, the pump, or the pump and motor, as the wireless energy is being transmitted, the apparatus adapted to at least one of:
transfer the wireless energy by a comprised energy transfer device into electric energy, to be used by any energy consuming parts of the apparatus, and
use the wireless energy directly for transferring it into kinetic energy thereby operating the operation device to operate of the restriction device.

11. The apparatus according to claim 1, further comprising a wireless remote control, an implantable switch, or a wireless remote control and an implantable switch, adapted to non-invasively control the hydraulic adjustment device, wherein the wireless remote control, the implantable switch, or the wireless remote control and the implantable switch is adapted to be manually controlled by the patient.

12. The apparatus according to claim 11, wherein the apparatus comprises the remote control, the remote control comprises a separate signal transmitter and receiver and, wherein the remote control is capable of obtaining information from implantable components of the apparatus and for commanding the hydraulic adjustment device to adjust the restriction device in response to obtained information.

13. The apparatus according to claim 1, wherein the hydraulic adjustment device comprises a fluid conduit, the reservoir forming part of the fluid conduit permitting movement of free fluid, said fluid conduit being void of any non-return valve between the reservoir and the restriction device, wherein the reservoir comprises a first wall portion adapted to be displaced in relation to a second wall portion of the reservoir thereby moving the free fluid void of any non-return valve between the reservoir and the restriction device.

14. The apparatus according to claim 1, further comprising implantable electrical components including at least one voltage level guard.

15. The apparatus according to claim 1, further comprising at least one of an implantable accumulator, a battery and an energiser adapted to be controlled from outside a body of the patient to supply energy to the hydraulic adjustment device and/or other implantable energy consuming components of the apparatus, wherein the first control unit is adapted to control at least one of, the implantable accumulator, the battery and the energiser unit to power a motor, a pump, or a motor and a pump with energy in response to a control signal.

16. The apparatus according to claim 15, wherein the at least one of, the implantable accumulator, the battery and the energiser and the apparatus further comprises a switch operable wireless energy adapted to be transmitted by an external transmitter, for connecting the at least one of, the implantable accumulator, the battery and the energiser to a signal receiver in an "on" mode when said switch is powered by the wireless energy and to keep the battery disconnected from the signal receiver in a "standby" mode when the switch is unpowered.

17. The apparatus according to claim 15, further comprising an external energy transmitter for transmitting wireless energy, the apparatus being adapted to charge the at least one of: the implantable accumulator, the battery and the energiser, using the wireless energy.

18. The apparatus according to claim 1, further comprising a pressure sensor for directly or indirectly sensing a pressure against the restriction device, wherein the restriction device is controlled in response to signals from the pressure sensor.

19. The apparatus according to claim 1, further comprising an external energy transmitter for transmitting wireless energy, wherein the wireless energy is transmitted by a signal comprising a wave signal comprising at least one of an electromagnetic wave signal, a sound wave signal and a carrier wave signal, wherein the apparatus is adapted to use the wireless energy by any energy consuming parts of the apparatus.

20. The apparatus according to claim 1, further comprising an energiser adapted to be controlled from outside the patient's body to supply energy to implantable energy consuming components of the apparatus, wherein the energiser comprises a capacitor.

21. A method for treating a patient suffering from anal incontinence by implanting an anal incontinence treatment apparatus according to claim 1, wherein the method step of placing the powered hydraulically operable non-inflatable restriction device in the patient, comprising the steps of:
cutting the skin of the patient,
inserting at least one dissecting tool,
dissecting an area of a fecal passageway using said at least one dissecting tool,
placing, in the patient, the powered hydraulically operable restriction device adapted to be energized by a source of energy,
placing said powered hydraulically operable restriction device in the dissected area,
placing the reservoir adapted to contain hydraulic fluid, and
forming a restricted fecal passageway, wherein the operable restriction device is adapted to be energized to open and close, respectively, the faecal passageway, adapted to be controlled from outside the patient's body by moving hydraulic fluid between the reservoir and the powered hydraulically operable restriction device and back, to restrict or release the powered hydraulically operable restriction device.

22. A method according to claim 21, wherein the method steps of, "cutting the skin of the patient" and "inserting at least one dissecting tool", comprising the steps of:
placing at least two laparascopic trocars in the patient's body,
inserting the at least one dissecting tool through at least one of the trocars,
inserting a camera for visual control, and
wherein the method step of dissecting an area of the fecal passageway involves using said the at least one dissecting tool inserted through said at least one trocars, dissecting said area of the fecal passageway.

* * * * *